United States Patent
Li et al.

(10) Patent No.: US 11,149,009 B2
(45) Date of Patent: Oct. 19, 2021

(54) FUSED PIPERIDINYL BICYCLIC AND RELATED COMPOUNDS AS MODULATORS OF C5A RECEPTOR

(71) Applicant: InflaRx GmbH, Jena (DE)

(72) Inventors: Yong Li, Ann Arbor, MI (US); Renfeng Guo, Ann Arbor, MI (US); Niels Christoph Riedemann, Jena (DE)

(73) Assignee: InflaRx GmbH, Jena (DE)

( * ) Notice: Subject to any disclaimer, the term of this patent is extended or adjusted under 35 U.S.C. 154(b) by 0 days.

(21) Appl. No.: 16/784,951

(22) Filed: Feb. 7, 2020

(65) Prior Publication Data
US 2020/0290969 A1  Sep. 17, 2020

Related U.S. Application Data

(60) Provisional application No. 62/873,612, filed on Jul. 12, 2019, provisional application No. 62/816,726, filed on Mar. 11, 2019.

(30) Foreign Application Priority Data

May 29, 2019  (EP) .................................. 19177349

(51) Int. Cl.
*C07D 215/54*  (2006.01)
*C07D 405/12*  (2006.01)

(52) U.S. Cl.
CPC ......... *C07D 215/54* (2013.01); *C07D 405/12* (2013.01)

(58) Field of Classification Search
None
See application file for complete search history.

(56) References Cited

U.S. PATENT DOCUMENTS

| 10,376,595 B2 | 8/2019 | Guo |
| 2007/0112015 A1 | 5/2007 | Hurt et al. |
| 2010/0160320 A1 | 6/2010 | Fan et al. |
| 2018/0282425 A1 | 10/2018 | Guo |
| 2020/0061202 A1 | 2/2020 | Guo |

FOREIGN PATENT DOCUMENTS

| CN | 108440513 A | 8/2018 |
| CN | 108440514 A | 8/2018 |
| CN | 108558844 A | 9/2018 |
| CN | 108727354 A | 11/2018 |
| CN | 108727355 A | 11/2018 |

OTHER PUBLICATIONS

Patani et al. "Bioisosterism: A Rational Approach In Drug Design" Chemical Reviews, 1996, vol. 96, pp. 3147-3176.*
International Search Report and Written Opinion in corresponding International Patent Application No. PCT/EP2020/053171, dated Jun. 15, 2020 (18 pages).
Klos et al., "International Union of Basic and Clinical Pharmacology. [corrected]. LXXXVII. Complement Peptide C5a, C4a, and C3a Receptors," Pharmacological Reviews, Jan. 2013, vol. 65, No. 1, pp. 500-543 (46 pages).
Li et al., "Neuroprotective effects of argatroban and C5a receptor antagonist (PMX53) following intracerebral haemorrhage," Clinical and Experimental Immunology, 2014, vol. 175, No. 2, pp. 285-295 (11 pages).
Merle et al., "Complement System Part I—Molecular Mechanisms of Activation and Regulation," Frontiers in Immunology, Jun. 2, 2015, vol. 6, Article No. 262, pp. 1-30 (30 pages).
Nunez-Cruz et al., "Genetic and Pharmacologic Inhibition of Complement Impairs Endothelial Cell Function and Ablates Ovarian Cancer Neovascularization," Neoplasia, Nov. 2012, vol. 14, No. 11, pp. 994-1004 (12 pages).
Ricklin et al., "The renaissance of complement therapeutics," Nature Reviews: Nephrology, Jan. 2018, vol. 14, No. 1, pp. 26-47 (22 pages).
Riedemann et al., "Controlling the anaphylatoxin C5a in diseases requires a specifically targeted inhibition," Clinical Immunology, 2017, vol. 180, pp. 25-32 (8 pages).
Schatz-Jakobsen et al., "Structural and functional characterization of human and murine C5a anaphylatoxins," Acta Crystallographica Section D Biological Crystallography, Jun. 2014, 70(Pt 6), pp. 1704-1717 (15 pages).
Tesar et al., "Avacopan in the treatment of ANCA-associated vasculitis," Expert Opinion on Investigational Drugs, 2018, vol. 27, No. 5, pp. 491-496 (6 pages).
Ciapetti et al., "Chapter 15—Molecular Variations Based on Isosteric Replacements," The Practice of Medicinal Chemistry (Third Edition), Jan. 1, 2008, pp. 290-342.
Database Integrity [Online] Clarivate Analytics; Sep. 20, 1995, Database Accession No. 226500.
Klos et al., "International Union of Basic and Clinical Pharmacology. [Corrected]. LXXXVII. Complement Peptide C5a, C4a, and C3a Receptors," Pharmacological Reviews, Jan. 2013, vol. 65, Iss. 1, pp. 500-543.
Li et al., "Neuroprotective effects of argatroban and C5a receptor antagonist (PMX53) following intracerebral haemorrhage," Clinical & Experimental Immunology, Feb. 2014, vol. 175, Iss. 2, pp. 285-295.
Merle et al., "Complement System Part I—Molecular Mechanisms of Activation and Regulation," Frontiers in Immunology, Jun. 2015, vol. 6, Article 262, pp. 1-30.
Nunez-Cruz et al., "Genetic and pharmacologic inhibition of complement impairs endothelial cell function and ablates ovarian cancer neovascularization," Neoplasia, Nov. 2012, vol. 14, No. 11, pp. 994-1004.
Ricklin et al., "The renaissance of complement therapeutics," Nature Reviews Nephrology, Jan. 2018, vol. 14, Iss. 1, pp. 26-47.
Riedemann et al., "Controlling the anaphylatoxin C5a in diseases requires a specifically targeted inhibition," Clinical Immunology, Jul. 2017, vol. 180, pp. 25-32.

(Continued)

*Primary Examiner* — Joseph R Kosack
(74) *Attorney, Agent, or Firm* — Melissa Hunter-Ensor; Scott Goncher; Greenberg Traurig, LLP

(57) ABSTRACT

The present invention relates to fused piperidinyl bicyclic, meta-substituted piperidinyl and their related compounds that modulate activities of mammalian C5a receptor by directly binding to the C5a receptor. The invention also relates to pharmaceutical compositions containing such compounds and their use in the treatment of a disease or a disorder involving pathogenic activation of C5a receptors.

2 Claims, 2 Drawing Sheets

(56) References Cited

OTHER PUBLICATIONS

Schatz-Jakobsen et al., "Structural and functional characterization of human and murine C5a anaphylatoxins," Acta Crystallographica Section D Biological Crystallography, Jun. 2014. vol. 70, Pt. 6, pp. 1704-1717.
Tesar et al., "Avacopan in the treatment of ANCA-associated vasculitis," Expert Opinion on Investigational Drugs, May 2018, vol. 27, Iss. 5, pp. 491-496.
Extended European Search Report issued in European Patent Application No. 19177349.8, dated Oct. 23, 2019 (6 pages).
Partial International Search Report issued in PCT Patent Application No. PCT/EP2020/053171, dated Apr. 21, 2020 (12 pages).

* cited by examiner

Route A

FUSED PIPERIDINYL BICYCLIC AND RELATED COMPOUNDS AS MODULATORS OF C5A RECEPTOR

CROSS-REFERENCE TO RELATED APPLICATIONS

This application claims the benefit of and priority to and the benefit of U.S. Provisional Application No. 62/816,726, filed on Mar. 11, 2019; European Patent Application No. EP19177349.8, filed on May 29, 2019; and U.S. Provisional Patent Application No. 62/873,612, filed on Jul. 12, 2019, each of which is incorporated herein in their entireties.

FIELD OF THE INVENTION

The present invention relates to fused piperidinyl bicyclic, meta-substituted piperidinyl and their related compounds that modulate activities of mammalian C5a receptor by directly binding to the C5a receptor. The invention also relates to pharmaceutical compositions containing such compounds and their use in the treatment of a disease or a disorder involving pathogenic activation of C5a receptors.

BACKGROUND OF THE INVENTION

C5a Generated by Activation of Complement System

The complement system is an important branch of innate immunity and plays a critical role in host defense against invading microbials. These functions are carried out by functionally-related proteins that sequentially detect, tag and eliminate pathogens and pathogen-affected cells. Complement proteins are primarily present in plasma of circulating blood to perform their immune surveillant functions. These proteins are inactive in steady state and are activated through enzyme cascades in response to infections, pathogenic mechanisms and artificial triggers, such as organ transplantations.

The complement proteins are activated by three canonical pathways that differ by initial activation mechanisms. The three pathways are the classical, alternative, and lectin-binding pathways. The classical pathway is activated by antibody complexes. The alternative pathway is initiated by foreign surfaces, such as certain molecules present on the membrane of microbials, altered host cell surfaces in lesions, artificial surfaces encountered during kidney dialysis. The lectin-binding pathway is triggered by the binding of mannose-binding lectin protein or ficolin to microbial carbohydrate structures. Upon initiation, the progression and amplification of all three pathways utilize the same underlying mechanism involving a cascade of enzymatic cleavage of complement proteins. All three pathways converge in the formation of C3 convertases, which result in proteolysis of C3 into bioactive fragments, C3a and C3b, which in turn lead to cleavage of C5 [1].

C5 is a 190 kDa protein comprising an alpha chain (~120 kDa) and a beta chain (~75 kDa). Enzymatic cleavage of the N-terminus of the alpha chain yields C5a. Human C5a is a globular protein with 74 amino acids, comprising a core structure and a flexible C-terminus. A saccharide chain conjugated to Asn residue at position 64 has a highly variable structure leading to molecular weight of human C5a ranging from 10 kDa to 15 kDa.

In addition to C5a, proteolysis of C5 also gives rise to C5b, which subsequently forms C5b-9 (MAC, membrane attack complex) with other complement components. C3a, C5a and MAC are terminal effectors of complement activation. MAC forms trans-cell membrane channels on pathogens or damaged host cells, leading to cell lysis. C3a and C5a are regarded as anaphylatoxins due to their potent proinflammatory effects, in which C5a is much more potent than C3a.

C5a Functions

C5a is a key driver for rapid innate immune responses to infections and injuries. C5a induces releases of histamine and TNF-alpha. C5a activates granulocytes. Particularly, C5a stimulates a spectrum of neutrophil activities. At lower concentrations, C5a is a potent chemoattractant of neutrophils. At higher concentrations, C5a induces the release of granular enzymes, the generation of oxidants by triggering oxidative burst. C5a stimulates production and release of pro-inflammatory cytokines, which in turn cause vasodilation, increase vascular permeability, and further enhance neutrophil extravasation. Neutrophils are a double-edged sword. On one hand, they defend against infections; on the other hand, they directly cause acute or chronic tissue damage when there is excessive activity of C5a.

C5a also plays a role in complex regulation of adaptive immunity. C5a is involved in the interactions between antigen-presenting cells and T cells. C5a can modulate T cell differentiation, survival, and proliferation. For instance, C5a-mediated priming and differentiation of Th-17 cell and IL-17 production have been proposed to be underlying mechanisms of some autoimmune diseases [2].

C5a Functions are Largely Mediated by C5a Receptor 1

C5a exerts its function via its cognate receptor, C5a receptor 1 (C5aR1), and later identified C5a receptor-like 2 (C5aR2). Both receptors consist of seven helical transmembrane domains and share approximately 35% homology in the primary sequence. C5aR1 is expressed by immune cells, including granulocytes and monocytes, as well as non-myeloid immune cells, such as T cells. C5aR1 is also found in non-immune cells in many organs, such as kidney, liver and lungs. C5aR1 is a G protein coupled receptor and linked to several G protein coupled downstream signaling transduction pathways, such as cAMP and calcium mediated pathways. Loss-of-function approaches including C5aR1 deficient animal models and pharmacological inhibition have shown that C5aR1 mediates multifaceted C5a functions in various pathophysiological contexts, which warrants the exercise of C5aR1 inhibitors, such as antibodies and antagonists, in pharmaceutical development and clinics with the goal to treat C5a-related disorders [3].

C5aR2 localizes both intracellularly and on the cell membrane. Because C5aR2 is not associated with G proteins, it was historically viewed as a non-functional decoy receptor and thus received much less attention compared with C5aR1. However, accumulating experimental observations have indicated that C5aR2 may have both pro- and anti-inflammatory effects depending on the biological contexts.

C5a-C5aR1 Axis is a Promising Therapeutic Target for Various Disorders.

C5a has been linked to a wide variety of diseases, including but not limited to: kidney-related disorders, cardiovascular disorders, respiratory diseases, skin disorders, arthritis, neurodegenerative disorders (Alzheimer's, dementia), ischemia-reperfusion injury, multiple sclerosis, transplant rejection, age-related macular degeneration, neutrophilic dermatoses, and cancer. In accordance with this view, preclinical and clinical data have highlighted the potential benefits of inhibiting C5a-C5aR1 interaction in several disorders [4-7].

Targeting C5a or C5a Receptors Versus Targeting C5 or C3.

In principle, there are multiple ways to block pathogenic C5a functions. It can be blocked by direct neutralizing C5a, such as using anti-C5a antibody, or by C5aR1 inhibitors. It can also be achieved by blocking C5a generation by inhibiting cleavage of C5, which can be achieved by targeting C5 per se or its upstream activators, such as C3. However, blocking C5a functions by targeting its upstream complement molecules is inherently confounded by the existence of extrinsic pathways. Extrinsic pathways refer to pathways other than the three canonic pathways that lead to cleavage of C5 and subsequent generation of C5a. Extrinsic pathways utilize a wide spectrum of proteases that are outside of complement realm. These proteases include proteases released by microbials, associated with coagulant cascade or activated during inflammatory responses and tissue damage [8].

Therefore, modalities targeting C3 or C5 do not block C5 cleavage by extrinsic pathways, and thus do not completely block C5a generation, which could lead to compromised therapeutic effects.

In addition, targeting C5a or C5a receptors versus targeting C5 and C3 has other potential clinical benefits. For instance, inhibiting C5 or C3 not only blocks C5a but also C5b and subsequent formation of MAC. Whereas targeting C5a or C5a receptors leaves MAC generation intact, which could be an advantage because MAC plays an important role in maintenance of homeostasis via its microbiocidal and tumoricidal effects. Clinical interventions targeting C5a or C5a receptors may carry less risks of infection complications than interventions targeting C5 or C3.

Technical Problems Underlying the Present Invention

As explained above, the C5a-C5aR1 axis is a promising therapeutic target for the treatment of various disorders. The present inventors have now been able to prepare novel compounds that directly target the C5a receptor, thereby avoiding the drawbacks associated with the targeting of C5 or C3.

The present invention describes the synthesis and biological potency of novel C5aR1 modulators. The compounds of the present invention exhibit high binding affinity to the C5a receptor and thus also high blocking activity for C5a-mediated physiological effects.

SUMMARY OF THE INVENTION

In a first aspect the present invention relates to a compound having the general formula (XXI)

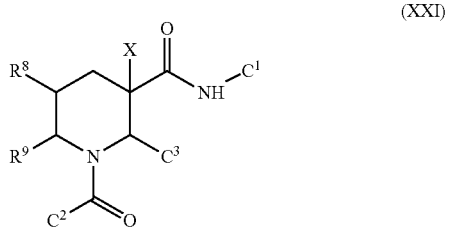

(XXI)

and pharmaceutically acceptable salts, hydrates and rotamers thereof;

wherein
$C^1$ is selected from the group consisting of aryl and heteroaryl, wherein the heteroaryl group has from 1-3 heteroatoms as ring members selected from N, O and S; and wherein said aryl and heteroaryl groups are optionally substituted with from 1 to 3 $R^1$ substituents;

$C^2$ is selected from the group consisting of aryl and heteroaryl, wherein the heteroaryl group has from 1-3 heteroatoms as ring members selected from N, O and S; and wherein said aryl and heteroaryl groups are optionally substituted with from 1 to 3 $R^2$ substituents;

$C^3$ is selected from the group consisting of $C_{1-8}$ alkyl or heteroalkyl, $C_{3-8}$ cycloalkyl, $C_{3-8}$ cycloalkyl-$C_{1-4}$ alkyl, aryl, aryl-$C_{1-4}$ alkyl, heteroaryl, heteroaryl-$C_{1-4}$ alkyl, heterocycloalkyl or heterocycloalkyl-$C_{1-4}$ alkyl, wherein the heteroalkyl group has from 1-3 heteroatoms selected from N, O and S, wherein the heterocycloalkyl group or portion has from 1-3 heteroatoms selected from N, O and S, and wherein the heteroaryl group has from 1-3 heteroatoms as ring members selected from N, O and S, and each $C^3$ is optionally substituted with from 1 to 3 $R^3$ substituents;

each $R^1$ is independently selected from the group consisting of halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^a$—C(O)$NR^aR^b$, —$NR^aC(O)NR^aR^b$, —$NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and is optionally substituted with one or two oxo; each $R^c$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl, and wherein the aliphatic and/or cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic or heterocyclic ring;

each $R^2$ is independently selected from the group consisting of halogen, —CN, —$NO_2$, —$R^f$, —$CO_2R^d$, —$CONR^dR^e$, —C(O)$R^d$, —OC(O)$NR^dR^e$, —$NR^eC(O)R^d$, —$NR^eC(O)_2R^f$, —$NR^dC(O)NR^dR^e$, —$NR^dR^e$, —$OR^d$, and —$S(O)_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and is optionally substituted with one or two oxo; each $R^f$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl, and wherein the aliphatic and/or cyclic portions of $R^d$, $R^e$ and $R^f$ are optionally further substituted with from one to three halogen, hydroxy, methyl, amino, alkylamino and dialkylamino groups, and optionally when two $R^2$ groups are on adjacent atoms, they are combined to form a five- or six-membered ring;

each $R^3$ is independently selected from the group consisting of halogen, —CN, —$R^i$, —$CO_2R^g$, —$CONR^gR^h$, —C(O)$R^g$, —C(O)$R^i$, —OC(O)$NR^gR^h$, —$NR^hC(O)R^g$, —$NR^hCO_2R^i$, —$NR^gC(O)NR^gR^h$, —$NR^gR^h$, —$OR^g$, —$OR^j$, —$S(O)_2NR^gR^h$, —$X^4$—$R^j$, —NH—$X^4$—$R^j$, —O—$X^4$—$R^j$, —$X^4$—$NR^gR^h$, —$X^4$—$NHR^j$, —$X^4$—

$CONR^gR^h$, $-X^4-NR^hC(O)R^g$, $-X^4-CO_2R^g$, $-O-X^r-CO_2R^g$, $-NH-X^4-CO_2R^g$, $-X^4-NR^hCO_2R^i$, $-O-X^4-NR^hCO_2R^i$, $-NHR^j$ and $-NHCH_2R^j$, wherein $X^4$ is a $C_{1-4}$ alkylene; each $R^g$ and $R^h$ is independently selected from hydrogen, $C_{1-8}$ alkyl or heteroalkyl, $C_{3-6}$ cycloalkyl and $C_{1-8}$ haloalkyl, or when attached to the same nitrogen atom can be combined with the nitrogen atom to form a four-, five- or six-membered ring having from 0 to 2 additional heteroatoms as ring members selected from N, O or S and is optionally substituted with one or two oxo; each $R^i$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl; and each $R^j$ is selected from the group consisting of $C_{3-6}$ cycloalkyl, imidazolyl, pyrimidinyl, pyrrolinyl, pyrrolyl, piperidinyl, morpholinyl, tetrahydrofuranyl, tetrahydropyranyl, and S,S-dioxo-tetrahydrothiopyranyl, and wherein the aliphatic and/or cyclic portions of $R^g$, $R^h$, $R^i$ and $R^j$ are optionally further substituted with from one to three halogen, methyl, $CF_3$, hydroxy, $C_{1-4}$ alkoxy, $C_{1-4}$ alkoxy-$C_{1-4}$ alkyl, $-C(O)O-C_{1-8}$ alkyl, amino, alkylamino and dialkylamino groups, and optionally when two $R^3$ groups are on adjacent atoms, they are combined to form a five- or six-membered ring; X is hydrogen or $CH_3$; and $R^8$ and $R^9$ are independently from each other selected from the group consisting of hydrogen, halogen, $C_1$-$C_8$ alkyl, $C_1$-$C_8$ haloalkyl, and $C_1$-$C_8$ alkoxy or $R^8$ and $R^9$ are combined to form a fused saturated or unsaturated mono- or multi-ring carbocycle in which one or more of the ring carbon atoms may be replaced independently from each other by N, S, or O, with the proviso that at least one of $R^8$ and $R^9$ is not hydrogen.

In a second aspect, the present invention relates to a pharmaceutical composition comprising a pharmaceutically acceptable carrier and a compound according to the first aspect.

In a third aspect, the present invention relates to a compound according to the first aspect for use in medicine.

In a fourth aspect, the present invention relates to a compound according to the first aspect for use in the treatment of a disease or disorder involving pathologic activation of C5a receptors.

This summary of the invention does not necessarily describe all features of the present invention. Other embodiments will become apparent from a review of the ensuing detailed description.

DETAILED DESCRIPTION OF THE INVENTION

Definitions

Figure 1:
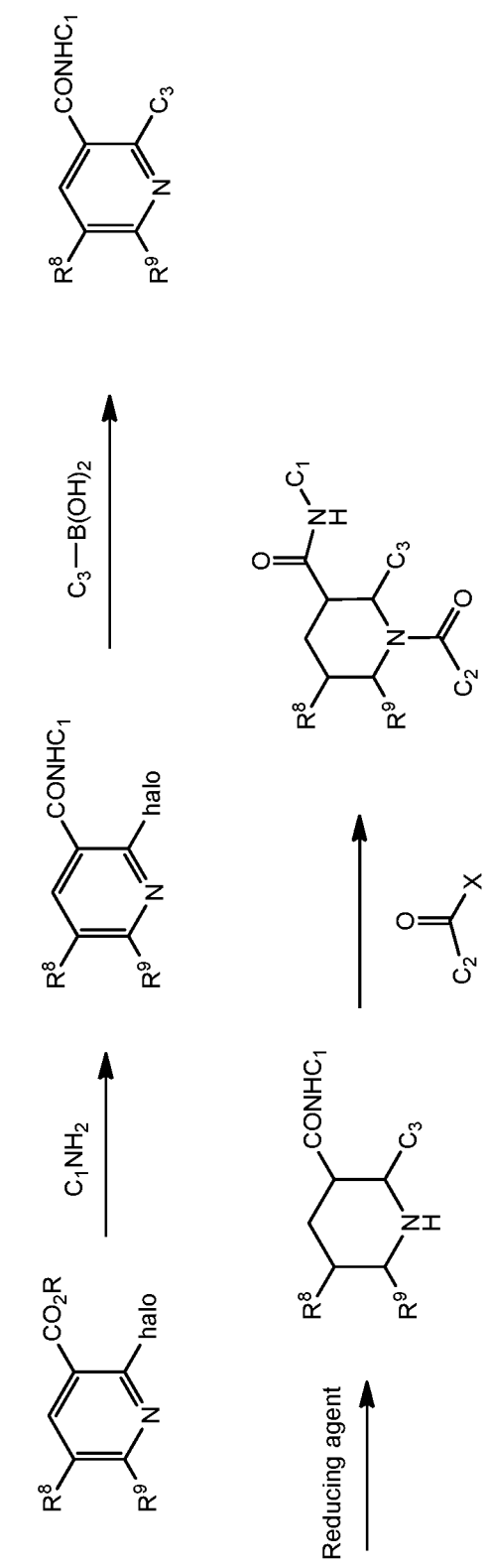
FIG. 1. General synthetic scheme for compounds of the invention. In general, compounds according of the invention are prepared by the general synthetic methods outlined in Route A.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents (for example: patents, patent applications, scientific publications, manufacturer's specifications, instructions, GenBank Accession Number sequence submissions etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the context of the present invention, C5a particularly refers to human C5a. The amino acid sequence of human C5 can be found under the accession number UniProtKB P01031 (CO5_HUMAN).

In the context of the present invention, the expression "C5a receptor" refers to any potential C5a binding ligand on the cell surface, especially to any receptor protein to which C5a may bind and elicit a reaction on said receptor (e.g. activation or inhibition of the receptor). The term "C5a receptor" particularly encompasses the two receptors C5aR and C5L2. Alternative names for C5aR are C5aR1 and CD88. An alternative name for C5L2 is C5aR2. Certain embodiments of the present invention refer to a compound modulating C5a receptor activity (e.g. by binding to a C5a receptor). In these contexts, the term "C5a receptor" can refer to (i) C5aR or to (ii) C5L2 or to (iii) both C5aR and C5L2. This means that some compounds modulate the activity of only one of the C5a receptors (i.e. either C5aR or C5L2), while other compounds modulate the activities of both C5a receptors (i.e. both C5aR and C5L2).

As used herein, a first compound (e.g. a compound of the invention) is considered to "bind" to a second compound (e.g. a target protein), if it has a dissociation constant $K_d$ to said second compound of 1 mM or less, preferably 100 µM or less, preferably 50 µM or less, preferably 30 µM or less, preferably 20 µM or less, preferably 10 µM or less, preferably 5 µM or less, more preferably 1 µM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

The term "binding" according to the invention preferably relates to a specific binding. "Specific binding" means that a compound (e.g. a protein ligand or nucleic acid aptamer) binds stronger to a target (e.g. a target protein or a target epitope) for which it is specific compared to the binding to another target. A compound binds stronger to a first target compared to a second target, if it binds to the first target with a dissociation constant ($K_d$) which is lower than the dissociation constant for the second target. Preferably the dissociation constant ($K_d$) for the target to which the compound binds specifically is more than 10-fold, preferably more than 20-fold, more preferably more than 50-fold, even more preferably more than 100-fold, 200-fold, 500-fold or 1000-fold lower than the dissociation constant ($K_d$) for the target to which the compound does not bind specifically.

As used herein, the term "$K_d$" (usually measured in "mol/L", sometimes abbreviated as "M") is intended to refer to the dissociation equilibrium constant of the particular interaction between a compound (e.g. a compound of the invention) and a target molecule.

Methods for determining binding affinities of compounds, i.e. for determining the dissociation constant $K_d$, are known to a person of ordinary skill in the art and can be selected for instance from the following methods known in the art: Surface Plasmon Resonance (SPR) based technology, Bio-layer interferometry (BLI), enzyme-linked immunosorbent assay (ELISA), flow cytometry, isothermal titration calorimetry (ITC), analytical ultracentrifugation, radioimmuno-assay (RIA or IRMA) and enhanced chemiluminescence (ECL). Typically, the dissociation constant $K_d$ is determined at 20° C., 25° C., 30° C., or 37° C. If not specifically indicated otherwise, the $K_d$ values recited herein are determined at 20° C. by SPR.

The term "naturally occurring", as used herein, as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

As used herein, a "patient" means any mammal or bird who may benefit from a treatment with the compound described herein (i.e. with an inhibitor of C5a receptor activity described herein). Preferably, a "patient" is selected from the group consisting of laboratory animals (e.g. mouse or rat), domestic animals (including e.g. guinea pig, rabbit, chicken, turkey, pig, sheep, goat, camel, cow, horse, donkey, cat, or dog), or primates including monkeys and apes (e.g. African green monkeys, chimpanzees, bonobos, gorillas) and human beings. It is particularly preferred that the "patient" is a human being. The terms "patient" and "subject to be treated" (or in short: "subject") are used interchangeably herein.

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease or disorder means preventing that a disorder occurs in a subject for a certain amount of time. For example, if a compound of the invention (or a pharmaceutical composition comprising the compound) is administered to a subject with the aim of preventing a disease or disorder, said disease or disorder is prevented from occurring at least on the day of administration and preferably also on one or more days (e.g. on 1 to 30 days; or on 2 to 28 days; or on 3 to 21 days; or on 4 to 14 days; or on 5 to 10 days) following the day of administration.

As used herein, "administering" includes in vivo administration, as well as administration directly to tissue ex vivo, such as vein grafts.

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

The term "alkyl", by itself or as part of another substituent, means, unless otherwise stated, a straight or branched chain hydrocarbon radical, having the number of carbon atoms designated (i.e. $C_1$-$C_8$ means one to eight carbons). The term "alkenyl" refers to an unsaturated alkyl group having one or more double bonds. Similarly, the term "alkynyl" refers to an unsaturated alkyl group having one or more triple bonds. The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings. The term "heterocycloalkyl" refers to a cycloalkyl group that contains from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycylic ring system. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, and S, and wherein the nitrogen and sulfur atoms may optionally be oxidized and the nitrogen heteroatom may optionally be quaternized. The heteroatom(s) O, N, and S may be placed at any interior position of the heteroalkyl group.

The term "heteroalkylene" by itself or as part of another substituent means a divalent radical, saturated or unsaturated or polyunsaturated, derived from heteroalkyl. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino," and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is meant to include trifluoromethyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include quinolinyl, quinolyl, isoquinolyl, and the like. Substituents for each of the above noted aryl and heteroaryl ring systems are selected from the group of acceptable substituents described below.

For brevity, the term "aryl" when used in combination with other terms (e.g.: aryloxy, arylthioxy, arylalkyl) includes both aryl and heteroaryl rings as defined above. Thus, the term "arylalkyl" is meant to include those radicals in which an aryl group is attached to an alkyl group.

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted versions, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted $C_{1-6}$ alkyl, unsubstituted heteroalkyl, unsubstituted aryl, aryl substituted with 1-3 halogens, unsubstituted $C_{1-6}$ alkyl, $C_{1-8}$ alkoxy or $C_{1-6}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. The term "acyl" as used by itself or as part of another group refers to an alkyl radical wherein two substituents on the carbon that is closest to the point of attachment for the radical is replaced with the substituent =O.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-6}$ alkyl, $C_{3-6}$ cycloalkyl, $C_{2-6}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), and sulfur (S).

As used herein, the term "CYCLE" means a saturated or unsaturated mono- or multi-ring carbocycle in which one or more (e.g. 1, 2, 3, or 4) of the ring carbon atoms may be replaced independently from each other by N, S, or O. The term "CYCLE" refers to fully saturated and unsaturated ring systems as well as partially unsaturated ring systems and is intended to include all the possible isomeric forms of the carbocycle (for example, pyrrolyl comprises 1H-pyrrolyl and 2H-pyrrolyl). Examples of where CYCLE is a monocyclic or bicyclic aryl group include phenyl and naphthyl. Examples of where CYCLE is a monocyclic or bicyclic cycloalkyl group include, but are not limited to, cyclopentyl and cyclohexyl. Examples of where CYCLE is a monocyclic or bicyclic saturated heterocycle include, but are not limited to, tetrahydrofuranyl, pyrrolidinyl, tetrahydrothienyl, piperidinyl, morpholinyl, thiomorpholinyl, piperazinyl and the like. Examples of where CYCLE is a monocyclic, bicyclic or tricyclic partially saturated heterocycle include, but are not limited to, pyrrolinyl, imidazolinyl, pyrazolinyl, and the like. Examples of where CYCLE is a monocyclic, bicyclic or tricyclic aromatic heterocycle include, but are not limited to, pyrrolyl, furanyl, thienyl, imidazolyl, oxazolyl, isoxazolyl, thiazolyl, isothiazolyl, pyrazolyl, pyridinyl, pyrimidinyl, pyrazinyl, pyridazinyl, triazinyl, and the like.

Throughout this specification, index numbers are used to distinguish different substituents in the compounds of the invention. Such index numbers are used as superscript numbers or as subscript numbers without denoting any particular meaning to the superscript or subscript usage. In other words, superscript index numbers and subscript index numbers are used interchangeably. For example, formulae (I), (XI) and (XXI) all contain the substituents C1, C2 and C3. In some formulae and reaction schemes, these substituents are shown as $C_1$, $C_2$, and $C_3$; in other formulae and reaction schemes, these substituents are shown as $C^1$, $C^2$, and $C^3$. But $C^1$ and $C_1$ is the same substituent; $C^2$ and $C_2$ is the same substituent; and $C^3$ and $C_3$ is the same substituent.

"Pharmaceutically acceptable" means approved by a regulatory agency of the Federal or a state government or listed in the U.S. Pharmacopeia or other generally recognized pharmacopeia for use in animals, and more particularly in humans.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds (for example $^2H$ (i.e. deuterium, D) in place of $^1H$). The compounds may also be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

EMBODIMENTS OF THE INVENTION

The present invention will now be further described. In the following passages different aspects of the invention are defined in more detail. Each aspect defined below may be combined with any other aspect or aspects unless clearly indicated to the contrary. In particular, any feature indicated as being preferred or advantageous may be combined with any other feature or features indicated as being preferred or advantageous.

In a first aspect the present invention is directed to a compound having the general formula (XXI)

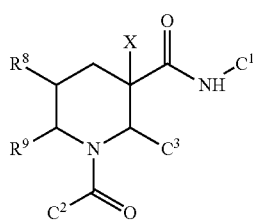

(XXI)

and pharmaceutically acceptable salts, hydrates and rotamers thereof;
wherein
- $C^1$ is selected from the group consisting of aryl and heteroaryl, wherein the heteroaryl group has from 1-3 heteroatoms as ring members selected from N, O and S; and wherein said aryl and heteroaryl groups are optionally substituted with from 1 to 3 $R^1$ substituents;
- $C^2$ is selected from the group consisting of aryl and heteroaryl, wherein the heteroaryl group has from 1-3 heteroatoms as ring members selected from N, O and S; and wherein said aryl and heteroaryl groups are optionally substituted with from 1 to 3 $R^2$ substituents;
- $C^3$ is selected from the group consisting of $C_{1-8}$ alkyl or heteroalkyl, $C_{3-8}$ cycloalkyl, $C_{3-8}$ cycloalkyl-$C_{1-4}$ alkyl, aryl, aryl-$C_{1-4}$ alkyl, heteroaryl, heteroaryl-$C_{1-4}$ alkyl, heterocycloalkyl or heterocycloalkyl-$C_{1-4}$ alkyl, wherein the heteroalkyl group has from 1-3 heteroatoms selected from N, O and S, wherein the heterocycloalkyl group or portion has from 1-3 heteroatoms selected from N, O and S, and wherein the heteroaryl group has from 1-3 heteroatoms as ring members selected from N, O and S, and each $C^3$ is optionally substituted with from 1 to 3 $R^3$ substituents;
- each $R^1$ is independently selected from the group consisting of halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^a$—C(O)$NR^aR^b$, —$NR^aC(O)NR^aR^b$, —$NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and is optionally substituted with one or two oxo; each $R^c$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl, and wherein the aliphatic and/or cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic or heterocyclic ring;
- each $R^2$ is independently selected from the group consisting of halogen, —CN, —$NO_2$, —$R^f$, —$CO_2R^d$, —$CONR^dR^e$, —C(O)$R^d$, —OC(O)$NR^dR^e$, —$NR^eC(O)R^d$, —$NR^eC(O)_2$ $R^f$, —$NR^dC(O)NR^dR^e$, —$NR^dR^e$, —$OR^d$, and —$S(O)_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and is optionally substituted with one or two oxo; each $R^f$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl, and wherein the aliphatic and/or cyclic portions of $R^d$, $R^e$ and $R^f$ are optionally further substituted with from one to three halogen, hydroxy, methyl, amino, alkylamino and dialkylamino groups, and optionally when two $R^2$ groups are on adjacent atoms, they are combined to form a five- or six-membered ring;
- each $R^3$ is independently selected from the group consisting of halogen, —CN, —$R^i$, —$CO_2R^g$, —$CONR^gR^h$, —C(O) $R^g$, —C(O)$R^i$, —OC(O)$NR^gR^h$, —$NR^hC(O)R^g$, —$NR^hCO_2R^i$, —$NR^gC(O)NR^gR^h$, —$NR^gR^h$, —$OR^g$, —$OR^j$, —$S(O)_2NR^gR^h$, —$X^4$—$R^j$, —NH—$X^4$—$R^j$, —O—$X^4$—$R^j$, —$X^4$—$NR^gR^h$, —$X^4$—$NHR^j$, —$X^4$—$CONR^gR^h$, —$X^4$—$NR^hC(O)R^g$, —$X^4$—$CO_2R^g$, —O—$X^4$—$CO_2R^g$, —NH—$X^4$—$CO_2R^g$, —$X^4$—$NR^hCO_2R^i$, —O—$X^4$—$NR^hCO_2R^i$, —$NHR^j$ and —$NHCH_2R^j$, wherein $X^4$ is a $C_{1-4}$ alkylene; each $R^g$ and $R^h$ is independently selected from hydrogen, $C_{1-8}$ alkyl or heteroalkyl, $C_{3-6}$ cycloalkyl and $C_{1-8}$ haloalkyl, or when attached to the same nitrogen atom can be combined with the nitrogen atom to form a four-, five- or six-membered ring having from 0 to 2 additional heteroatoms as ring members selected from N, O or S and is optionally substituted with one or two oxo; each $R^i$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl; and each $R^j$ is selected from the group consisting of $C_{3-6}$ cycloalkyl, imidazolyl, pyrimidinyl, pyrrolinyl, pyrrolyl, piperidinyl, morpholinyl, tetrahydrofuranyl, tetrahydropyranyl, and S,S-dioxo-tetrahydrothiopyranyl, and wherein the aliphatic and/or cyclic portions of $R^g$, $R^h$, $R^i$ and $R^j$ are optionally further substituted with from one to three halogen, methyl, $CF_3$, hydroxy, $C_{1-4}$ alkoxy, $C_{1-4}$ alkoxy-$C_{1-4}$ alkyl, —C(O)$OC_{1-8}$ alkyl, amino, alkylamino and dialkylamino groups, and optionally when two $R^3$ groups are on adjacent atoms, they are combined to form a five- or six-membered ring;
- X is hydrogen or $CH_3$; and
- $R^8$ and $R^9$ are independently from each other selected from the group consisting of hydrogen, halogen, $C_1$-$C_8$ alkyl, $C_1$-$C_8$ haloalkyl, and $C_1$-$C_8$ alkoxy or $R^8$ and $R^9$ are combined to form a fused saturated or unsaturated mono- or multi-ring carbocycle in which one or more of the ring carbon atoms may be replaced independently from each other by N, S, or O, with the proviso that at least one of $R^8$ and $R^9$ is not hydrogen.

In some embodiments of the first aspect, X is hydrogen.

In some embodiments of the first aspect, the compound has formula (XXIa)

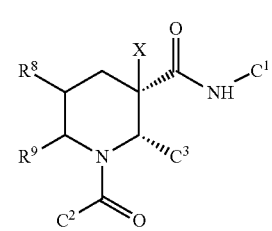

(XXIa)

In some embodiments of the first aspect, the compound has formula (Ia) or formula (XI):

(I)

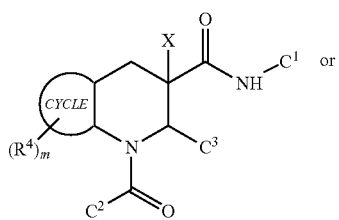

or (XI)

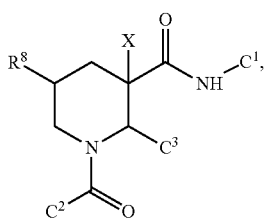

wherein

X, C¹, C², and C³ are defined as above;

R⁸ in Formula (XI) is also defined as above [which means that R⁸ is selected from the group consisting of halogen, $C_1$-$C_8$ alkyl, $C_1$-$C_8$ haloalkyl, and $C_1$-$C_8$ alkoxy, because in Formula (XI) R⁹ is hydrogen and therefore not explicitly shown so that the R⁸ cannot be hydrogen due to the proviso recited above and so that R⁸ and R⁹ cannot combine to form a fused saturated or unsaturated mono- or multi-ring carbocycle];

R⁴ is selected from the group consisting of cyano, halo, nitro, hydroxyl, ($C_1$-$C_6$)alkyl, ($C_3$-$C_6$)cycloalkyl, ($C_1$-$C_6$) alkyl-OH, ($C_1$-$C_6$)-alkyl-NR⁵R⁶, trifluoromethyl, ($C_1$-$C_6$) alkoxy, ($C_1$-$C_6$)thioalkoxy, phenoxy, COR⁷, NR⁵R⁶, NHCO($C_1$-$C_6$) alkyl, SO₃H, SO₂($C_1$-C6) alkyl and SO₂NR⁵R⁶;

R⁵ and R⁶ are each independently selected from the group consisting of hydrogen, ($C_1$-$C_6$)alkyl and ($C_3$-$C_6$)cycloalkyl;

R⁷ is independently hydroxyl, ($C_1$-$C_6$)alkoxy, phenoxy or —NR⁵R⁶;

m is 0-4; and

CYCLE is a saturated or unsaturated mono- or multi-ring carbocycle in which one or more of the ring carbon atoms may be replaced independently from each other by N, S, or O.

In further embodiments of the first aspect, the compound has formula (Ia) or formula (XIa):

(Ia)

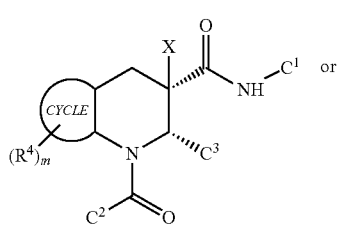

or (XIa)

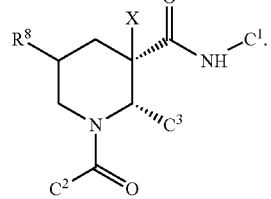

In some embodiments of the first aspect, CYCLE is a saturated or unsaturated mono- or multi-ring carbocycle in which from one to four (preferably from 1 to 3, more preferably 1 or 2, even more preferably 1) of the ring carbon atoms may be replaced independently from each other by N, S, or O.

In some embodiments of the first aspect, the compound has formula (II):

(II)

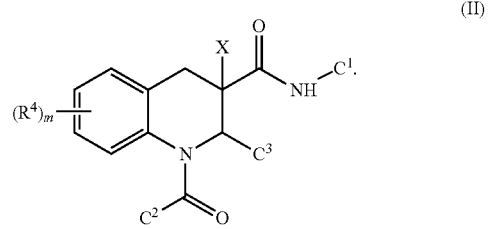

In further embodiments of the first aspect, the compound has formula (IIa):

(IIa)

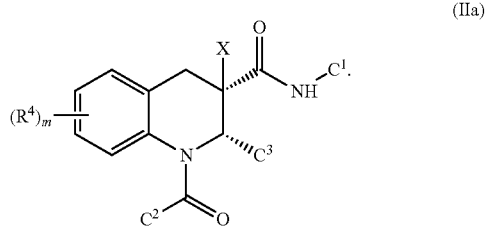

In some embodiments of the first aspect, the compound has a formula selected from the group consisting of (IIIa), (IIIb), (IIIc), and (IIId):

(IIIa)

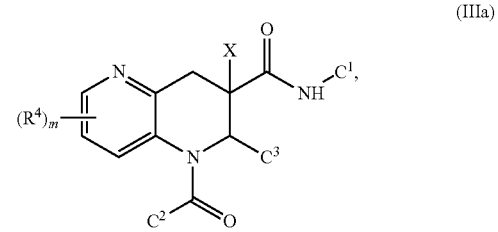

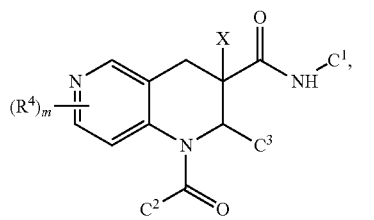
(IIIb)

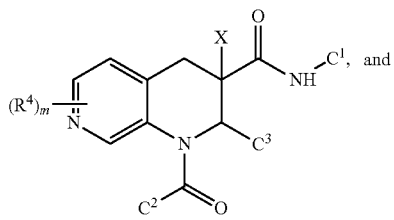
(IIIc)

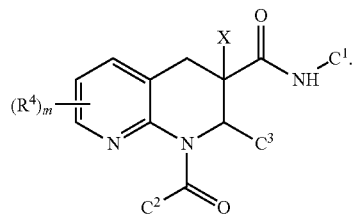
(IIId)

In further embodiments, the integer m is 0. In these embodiments, there is no substituent $R^4$.

In further embodiments of the first aspect, the compound has a formula selected from the group consisting of (IIIe), (IIIf), (IIIg), and (IIIh):

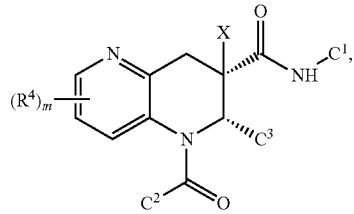
(IIIe)

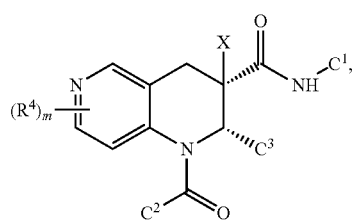
(IIIf)

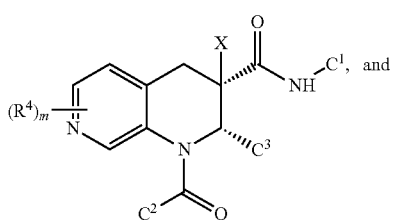
(IIIg)

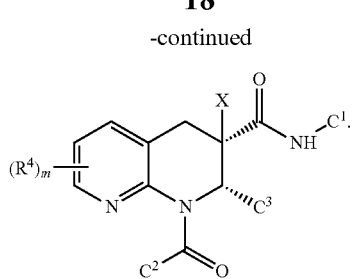
(IIIh)

In further embodiments, the integer m is 0, i.e. in these embodiments, there is no substituent $R^4$.

In some embodiments of the first aspect, $C^1$ is

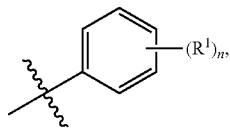

wherein
$R^1$ is defined as above, and
n is an integer selected from 0, 1, 2, or 3, preferably 2.

In further embodiments, each $R^1$ is independently selected from the group consisting of —OH, halogen, $C_{1-6}$ alkyl, hydroxy ($C_{1-6}$) alkyl, and halo ($C_{1-6}$) alkyl. In preferred embodiments, each $R^1$ is independently selected from the group consisting of —OH, chloro, methyl, —CH$_2$—OH, and CF$_3$.

In some embodiments of the first aspect, $C^2$ is

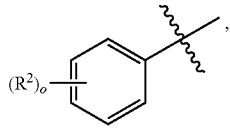

wherein
$R^2$ is defined as above, and
o is an integer selected from 0, 1, 2, or 3.

In further embodiments, each $R^2$ is independently selected from the group consisting of $C_{1-6}$ alkyl and halogen. In preferred embodiments, each $R^2$ is independently selected from the group consisting of methyl, fluoro, and chloro.

In some embodiments of the first aspect, $C^3$ is

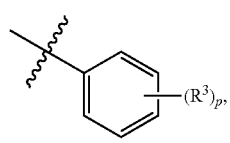

wherein
$R^3$ is defined as above, and
p is an integer selected from 0, 1, 2, or 3.

In preferred embodiments, p is 1 and $R^3$ is $C_1$-$C_8$ hydroxyalkyl (preferably hydroxypentyl), $C_1$-$C_8$ hydroxyalkoxy (preferably hydroxybutoxy), or NHR$^j$ as defined above. In further preferred embodiments, R$^j$ is selected from the group consisting of $C_1$-$C_8$ alkyl, $C_1$-$C_8$ hydroxyalkyl, $C_3$-$C_6$ cycloalkyl and tetrahydropyranyl. In further preferred embodiments, $R^j$ is selected from the group consisting of isopropyl, hydroxybutyl, cyclobutyl, cyclopentyl and tetrahydropyranyl.

In some embodiments of the first aspect, $R_8$ is selected from the group consisting of halogen, $C_1$-$C_4$ alkyl, $C_1$-$C_4$ haloalkyl, and $C_1$-$C_4$ alkoxy. In preferred embodiments, $R_8$ is selected from the group consisting of fluoro, chloro, methyl, trifluoromethyl, and methoxy.

In some embodiments of the first aspect, the compound is selected from the group consisting of INF004, INF011, INF014, INF015, INF022, INF023, INF024, INF025, INF030, INF033, INF034, INF035, INF038, INF039, INF040, INF041, INF045, INF046, INF047, INF048, INF049, INF050, INF051, INF052, INF053, INF055, INF056, INF058, INF067, INF068, INF069, INF070, INF071, INF072, INF075, INF077, and INF080. The structural formulas and the chemical names of these compounds are shown below in chapter "C. Results" of the Example section.

It is preferred that the compounds according to the first aspect of the invention have an $IC_{50}$ of 1 µM or lower in a $Ca^{2+}$ mobilization assay. $Ca^{2+}$ mobilization assays are well known in the art. A preferred $Ca^{2+}$ mobilization assay uses human monocytes like, e.g. U-937 (ATCC® CRL-1593.2™). A $Ca^{2+}$ mobilization assay suitable to determine the $IC_{50}$ is described in the Examples. Preferably the compounds has an $IC_{50}$ of 500 nM or lower, more preferably of 200 nM or lower and even more preferably of 100 nM or lower in a $Ca^{2+}$ mobilization assay.

In a second aspect, the present invention is directed to a pharmaceutical composition comprising a pharmaceutically acceptable carrier and a compound according to the first aspect.

In some embodiments of the second aspect, the pharmaceutical composition further comprises one or more pharmaceutically acceptable diluents, excipients, fillers, binders, lubricants, glidants, disintegrants, adsorbents, and/or preservatives.

In a third aspect, the present invention is directed to a compound according to the first aspect for use in medicine.

In a fourth aspect, the present invention is directed to a compound according to the first aspect for use in the treatment of a disease or disorder involving pathologic activation of a C5a receptor.

In an alternative wording, the fourth aspect of the present invention is directed to the use of a compound according to the first aspect for the preparation of a pharmaceutical composition for the treatment of a disease or disorder involving pathologic activation of a C5a receptor.

In another alternative wording, the fourth aspect of the present invention is directed to a method for the treatment of a disease or disorder involving pathologic activation of a C5a receptor, wherein said method comprises the step of administering a therapeutic amount of a compound according to the first aspect to a subject in need of such treatment.

In some embodiments of the fourth aspect, the disease or disorder involving pathologic activation of a C5a receptor is selected from the group consisting of
  autoimmune disorders,
  inflammatory disorders or related conditions,
  cardiovascular or cerebrovascular disorders,
  HIV infection or AIDS,
  neurodegenerative disorders or related diseases, and
  cancers or precancerous conditions.

Pharmaceutical Compositions and Modes of Administration

In the practice of any aspect of the present invention, a compound described herein or a pharmaceutical composition comprising the compound may be administered to a patient by any route established in the art which provides a sufficient level of the compound in the patient. It can be administered systemically or locally. Such administration may be parenterally, transmucosally, e.g., orally, nasally, rectally, intravaginally, sublingually, submucosally, transdermally, or by inhalation. Preferably, administration is parenteral, e.g., via intravenous or intraperitoneal injection, and also including, but is not limited to, intra-arterial, intramuscular, intradermal and subcutaneous administration. If the compound described herein or a pharmaceutical composition comprising the compound is administered locally, it can be injected directly into the organ or tissue to be treated.

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. Pharmaceutical compositions may also be administered via the nasal cavity to the lungs.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets.

In a preferred embodiment, a compound described herein is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

In another embodiment, for example, a compound described herein or a pharmaceutical composition comprising the compound can be delivered in a controlled-release system. For example, the compound may be administered using intravenous infusion, an implantable osmotic pump, a transdermal patch, liposomes, or other modes of administration. In one embodiment, a pump may be used (see Sefton (1987) CRC Crit. Ref. Biomed. Eng. 14: 201; Buchwald et al. (1980) Surgery 88:507; Saudek et al. (1989) N. Eng. J. Med. 321: 574). In another embodiment, the compound can be delivered in a vesicle, in particular a liposome (see Langer (1990) Science 249:1527-1533; Treat et al. (1989) in Liposomes in the Therapy of Infectious Disease and Cancer, Lopez-Berestein and Fidler (eds.), Liss, N.Y., 353-365; WO 91/04014; U.S. Pat. No. 4,704,355). In another embodiment, polymeric materials can be used (see Medical Applications of Controlled Release (1974) Langer and Wise (eds.), CRC Press: Boca Raton, Fla.; Controlled Drug Bioavailability, Drug Product Design and Performance, (1984) Smolen and Ball (eds.), Wiley: N. Y.; Ranger and Peppas (1953) J. Macromol. Sci. Rev. Macromol. Chem. 23: 61; see also Levy et al. (1985) Science 228:190; During et al. (1989) Ann. Neurol. 25: 351; Howard et al. (1989) J. Neurosurg. 71: 105).

In yet another embodiment, a controlled release system can be placed in proximity of the therapeutic target, i.e., the target cells, tissue or organ, thus requiring only a fraction of the systemic dose (see, e.g., Goodson (1984) 115-138 in Medical Applications of Controlled Release, vol. 2). Other controlled release systems are discussed in the review by Langer (1990, Science 249: 1527-1533).

In a specific embodiment, it may be desirable to administer a compound described herein or a pharmaceutical composition comprising the compound locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as Silastic™ membranes, or fibers.

Selection of the preferred effective dose will be determined by a skilled artisan based upon considering several factors which will be known to one of ordinary skill in the art. Such factors include the particular form of the pharmaceutical composition, e.g. polypeptide or vector, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be prevented and or treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, according to standard clinical techniques.

Methods of preparing various pharmaceutical compositions with a certain amount of active ingredient are known to those skilled in the art. For examples of methods of preparing pharmaceutical compositions, see Remington: The Science and Practice of Pharmacy, Lippincott, Williams & Wilkins, 21st ed. (2005).

In one embodiment of the invention, the compounds of the invention may also be combined with at least one additional therapeutic agent.

General Chemical Process Procedures and Description of Drawings

In general, compounds of the present invention are prepared by the general synthetic methods outlined in Route A (see FIG. 1).

With regards Route A, the corresponding acid can be coupled with an amine utilizing a coupling agent such as HATU and a base such as diisopropylethylamine or using thionyl chloride and a base such as diisopropylamine in a solvent such as dichloromethane. Coupling at the two position of the pyridine ring can be accomplished via a Suzuki-type coupling reaction with a suitably substituted halo pyridine derivative and a suitably substituted boronic acid utilizing transition metal catalysis and a base such as potassium carbonate in solvents such as aqueous DMF or toluene. Hydrogenation with a reducing agent such as hydrogen gas and a platinum catalyst in solvents such as ethanol, gives the required piperidine. Absolute stereochemistry may be set by a variety of methods, via the use of chiral ligands or a chiral auxiliary, separation of chiral diastereomers, use of chiral starting materials, or classical resolution. Acylation of the piperidine can be accomplished by utilizing a suitably substituted acyl derivative where X may be chosen from an appropriate group such as OH, Cl and F, or from any group capable of activating a carbonyl group for addition of an amine (e.g. imidazole). Such couplings may be assisted by the use of inorganic or organic bases, activating agents such as HBTU, and also by catalysts such as DMAP, HOBT, etc. Final compounds can be isolated by the use of chiral chromatography techniques such as supercritical fluid chromatography (SFC) where the mobile phase is a supercritical fluid such as carbon dioxide with cosolvents such as methanol, ethanol or isopropanol.

Figure 2:
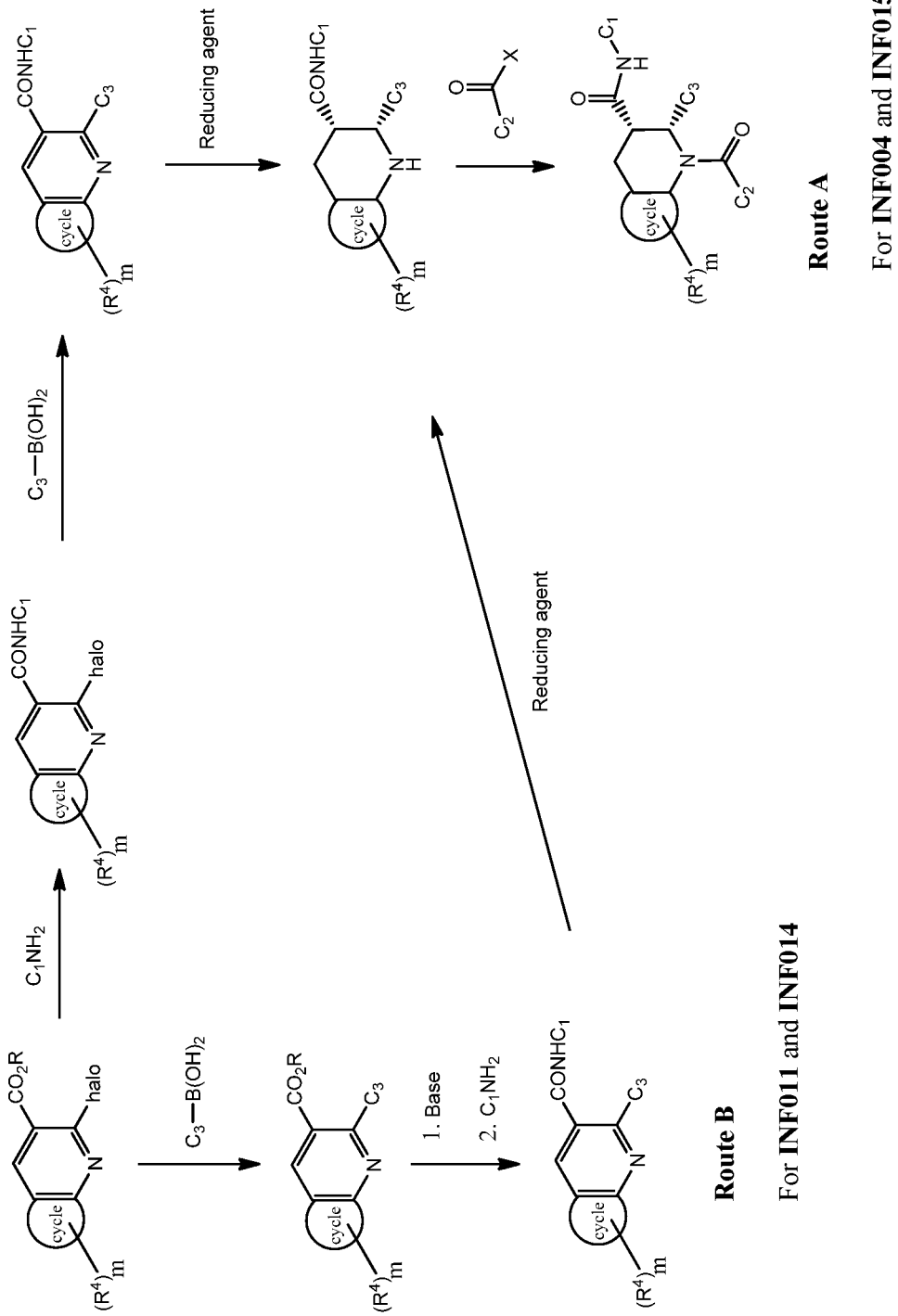
FIG. 2. General synthetic scheme for compounds according to formula (I). In general, compounds according to formula (I) can be prepared by the general synthetic methods outlined in Route A or in Route B.

Compounds according to general formula (I) may be prepared by the general synthetic methods outlined in Routes A or B (see FIG. 2).

Route A shown in FIG. 2 is almost identical to Route A shown in FIG. 1. However, the hydrogenation step in FIG. 2 can also be performed with a reducing agent such as sodium cyanoborohydride in solvents such as THF and methanol, yielding the desired 2,3-cis piperidine.

With regards Route B, coupling at the two position of the pyridine ring can be accomplished via a Suzuki-type coupling reaction with a suitably substituted halo pyridine derivative and a suitably substituted boronic acid utilizing transition metal catalysis and a base such as sodium carbonate in solvents such as aqueous DMF or toluene. Hydrolysis of the resulting ester with a base such as lithium hydroxide in a solvent such as aqueous THF yields the corresponding acid which can then be coupled with an amine utilizing a coupling agent such as HATU and a base such as diisopropylethylamine or NMM in a solvent such as DMF. Hydrogenation with a reducing agent such as sodium cyanoborohydride in solvents such as THF and methanol, gives the required 2,3-cis piperidine. Absolute stereochemistry may also be set by a variety of methods, via the use of chiral ligands or a chiral auxiliary, separation of chiral diastereomers, use of chiral starting materials, or classical resolution. Acylation of the piperidine can be accomplished by utilizing a suitably substituted acyl derivative where X may be chosen from an appropriate group such as OH, Cl and F, or from any group capable of activating a carbonyl group for addition of an amine (e.g. imidazole). Such couplings may be assisted by the use of inorganic or organic bases, activating agents such as HBTU, and also by catalysts such as DMAP, HOBT, etc. Those skilled in the art will recognize that there are other possible combinations which will also result in the desired product. Final compounds can be isolated by the use of chiral chromatography techniques such as supercritical fluid chromatography (SFC) where the mobile phase is a supercritical fluid such as carbon dioxide with cosolvents such as methanol, ethanol or isopropanol.

EXAMPLES

The following examples are offered to illustrate, but not to limit the claimed invention. Compounds within the scope of this invention can be synthesized as described below, using a variety of reactions known to the skilled artisan. One skilled in the art will also recognize that alternative methods may be employed to synthesize the target compounds of this invention and that the approaches described within the body of this document are not exhaustive, but do provide broadly applicable and practical routes to compounds of interest. Certain molecules claimed in this patent can exist in different enantiomeric and diastereomeric forms and all such variants of these compounds are claimed. The detailed description of the experimental procedures used to synthesize key compounds in this text lead to molecules that are described by the physical data identifying them as well as by the structural depictions associated with them. Those skilled in the art will also recognize that during standard work up procedures, acids and bases are frequently used. Salts of the parent compounds are sometimes produced.

A. Chemical Synthesis Protocols

Example 1

Synthesis of (2R,3S)-2-(4-(cyclopentylamino)phenyl)-1-(2-fluoro-6-methylbenzoyl)-N-(4-methyl-3-(trifluoromethyl)phenyl)-1,2,3,4-tetrahydroquinoline-3-carboxamide (INF004)

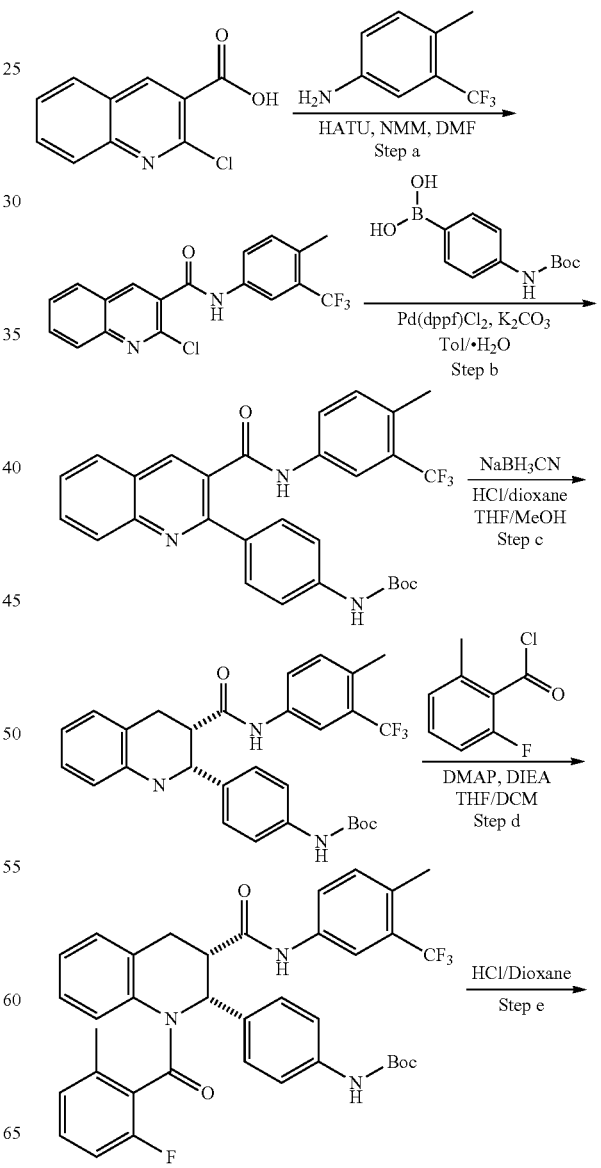

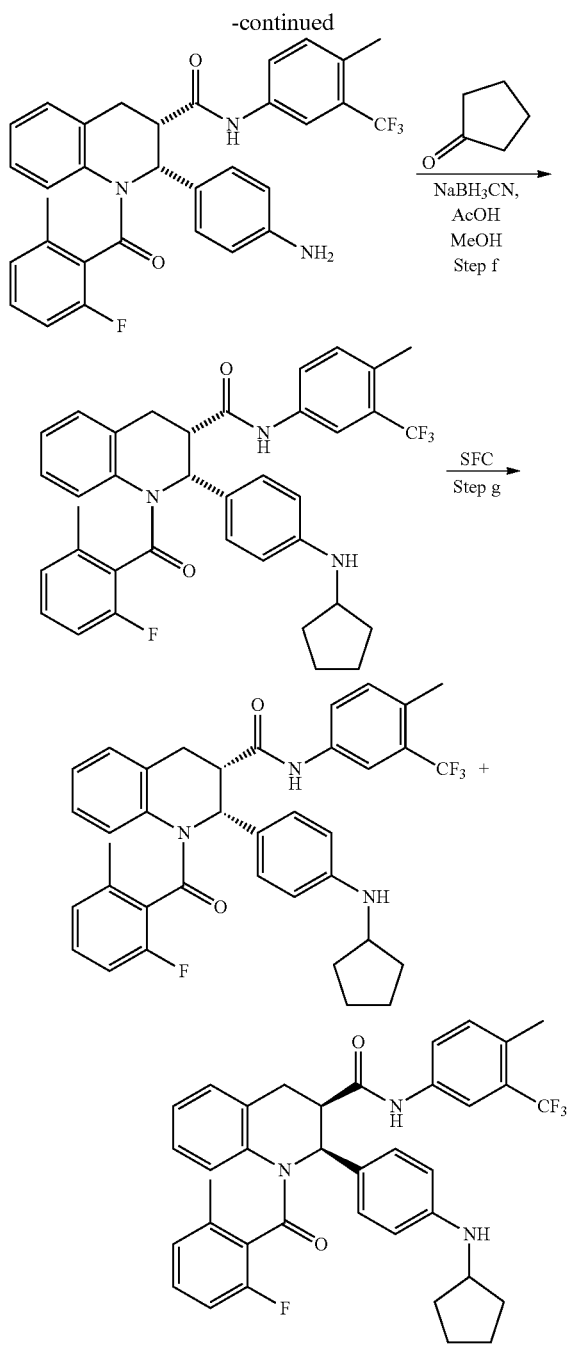

a) To a solution of compound 2-chloroquinoline-3-carboxylic acid (1.00 g, 4.82 mmol), 4-methyl-3-(trifluoromethyl)aniline (1.27 g, 7.22 mmol, 1.04 mL) and NMM (1.46 g, 14.5 mmol, 1.59 mL) in DMF (10.0 mL) was added HATU (3.66 g, 9.63 mmol). The reaction mixture was stirred at 25° C. for 1 hr. The reaction mixture was diluted with water (100 mL), extracted with EtOAc (200 mL×2). The organic phase was separated, dried over Na$_2$SO$_4$, filtered and concentrated in vacuum. The residue was purified by silica gel chromatography (Petroleum ether:EtOAc=8:1~2:1) to give 2-chloro-N-(4-methyl-3-(trifluoromethyl)phenyl)quinoline-3-carboxamide (1.95 g, 4.12 mmol, 85.5% yield) as a white solid. LCMS: R$_t$=0.889 min, MS+1=365.0. $^1$H NMR: 400 MHz DMSO-d6 δ 11.0 (s, 1H), 8.79 (s, 1H), 8.16-8.15 (m, 2H), 8.06 (d, J=8.0 Hz, 1H), 7.96-7.84 (m, 1H), 7.79-7.73 (m, 1H), 7.49-7.47 (m, 1H), 2.44 (s, 3H) ppm.

b) To a mixture of compound 2-chloro-N-(4-methyl-3-(trifluoromethyl)phenyl)quinoline-3-carboxamide (550 mg, 1.51 mmol), (4-((tert-butoxycarbonyl)amino)phenyl)boronic acid (530 mg, 2.24 mmol) and K$_2$CO$_3$ (625 mg, 4.52 mmol) in H$_2$O (2.00 mL) and toluene (20.0 mL) was added Pd(dppf)Cl$_2$ (221 mg, 302 μmol). The reaction mixture was stirred at 100° C. for 10 hrs. The reaction was diluted with EtOAc (200 mL) and filtered through a pad of celite. The filtrate was concentrated in vacuum to give tert-butyl (4-(3-((4-methyl-3-(trifluoromethyl)phenyl)carbamoyl)quinolin-2-yl)phenyl)carbamate (2.90 g, crude) as a gray solid which was used directly in next step. LCMS: R$_t$=1.130 min, MS+1=522.2 c) To a solution of tert-butyl (4-(3-((4-methyl-3-(trifluoromethyl)phenyl)carbamoyl)-quinolin-2-yl)phenyl)carbamate (2.20 g, 4.22 mmol) in THF (7.00 mL) and MeOH (3.50 mL) was added NaBH$_3$CN (3.92 g, 62.4 mmol). The reaction mixture was adjusted to pH=4~6 with 4 N HCl/dioxane and the mixture was stirred at 20° C. for 0.5 hr. TLC (Petroleum ether:EtOAc=3:1) showed the reaction was completed and two spots (R$_f$=0.6, 0.65) were found. The reaction mixture was adjusted to pH=7~8 with saturated NaHCO$_3$, diluted with water (200 mL), extracted with EtOAc (120 mL×2). The organic phase was separated, dried over Na$_2$SO$_4$, filtered and concentrated in vacuum. The residue was triturated with petroleum ether:EtOAc=10:1 (15.0 mL) at 0° C. to give the cis product (350 mg, 666 μmol, 15.8% yield) as a white solid which was used directly in next step.

d) To a solution of the product obtained above (350 mg, 666 μmol), DIEA (522 mg, 4.04 mmol, 704 μL,) and DMAP (10 mg, 81.9 μmol) in DCM (10.0 mL) and THF (2.00 mL) was added 2-fluoro-6-methylbenzoyl chloride (350 mg, 2.03 mmol) at 20° C. The reaction mixture was stirred at 20° C. for 2 hrs. Then more 2-fluoro-6-methylbenzoyl chloride (350 mg, 2.03 mmol) and DIEA (522 mg, 4.04 mmol, 704 μL) was added and the mixture was stirred at 20° C. for another 1 hr. LCMS showed ~19.0% of the cis compound (R$_t$=0.953 min, MS+1=526.1) remained along with the desired compound (MS (R$_t$=0.996 min, MS−56+1=606.2. The reaction was quenched by water (20.0 mL), extracted with EtOAc (20.0 mL×2). The organic phase was washed with brine (50.0 mL), separated, dried over Na$_2$SO$_4$, filtered and concentrated in vacuum. The residue was purified by Prep. HPLC (0.1% TFA) to give the desired compound (151 mg, 33.9% yield) as a yellow solid which was checked by HPLC R$_t$=2.799 min and LCMS R$_t$=0.996 min, MS−55=606.0.

e) To a solution of the compound obtained in step d) (150 mg, 227 μmol) in EtOAc (2.00 mL) was added HCl/dioxane (4 M, 8.57 mL). The reaction mixture was stirred at 20~25° C. for 0.5 hr. LCMS showed the reaction was complete and the desired MS (R$_t$=0.836 min, MS+1=562.0) was found. The reaction was concentrated in vacuum. The residue was dissolved in water (20.0 mL), adjusted to pH=8 with saturated NaHCO$_3$, extracted with EtOAc (25.0 mL×2). The organic phase was separated, washed with brine (50.0 mL), dried over Na$_2$SO$_4$, filtered and concentrated in vacuum to give the desired compound (129 mg, crude) as a yellow solid which was checked by HPLC R$_t$=2.134 min. and Super Critical Fluid chromatography (SFC) (two peaks at 1.231 and 1.521 min).

f) To a mixture of the compound obtained in step e) (60 mg, 107 μmol) and cyclopentanone (60 mg, 713 μmol, 63.2 μL) in MeOH (1.50 mL) was added AcOH (8 mg, 133 μmol, 7.62 μL). The reaction mixture was stirred at 30° C. for 1 hr. Then NaBH₃CN (35 mg, 557 μmol) was added and the mixture was stirred at 30° C. for 1 hr. LCMS showed the desired compound was obtained (R$_f$=0.893 min, MS+1=630.1). The reaction mixture was concentrated in vacuum. The residue was diluted with EtOAc (30.0 mL), washed with water (50.0 mL). The organic phase was separated, dried over Na₂SO₄, filtered and concentrated in vacuum. The residue was purified by Prep.TLC (Petroleum ether:EtOAc=2:1) to give the desired compound (40 mg, 60.9 μmol, 57.0% yield, 95.8% purity) as a white solid which was checked by HPLC R$_t$=2.422 min. and Super Critical Fluid chromatography (SFC) (two peaks at 1.780 min and 2.581 min.).

g) The compound obtained above (60 mg, 95.29 μmol) was purified by Prep.SFC (column: REGIS (s,s) WHELK-O1 (250 mm*50 mm, 10 μm); mobile phase: [0.1% NH₃H₂O MEOH]; B %: 35%-35%, 3.3 min; 30 min) to give (2R,3S)-2-(4-(cyclopentylamino)phenyl)-1-(2-fluoro-6-methylbenzoyl)-N-(4-methyl-3-(trifluoromethyl)phenyl)-1,2,3,4-tetrahydroquinoline-3-carboxamide (6.38 mg, 20.8% yield, 97.8% purity) as an off-white solid. ¹H NMR: 400 MHz MeOD δ 7.67-7.26 (m, 2H), 7.23-7.03 (m, 6H), 6.92-6.78 (m, 3H), 6.77-6.55 (m, 2H), 6.47-6.28 (m, 3H), 3.59-3.52 (m, 2H), 3.45-3.03 (m, 1H), 3.21-3.03 (m, 1H), 2.65-2.15 (m, 5.5H), 1.91-1.65 (m, 3.5H), 1.64-1.57 (m, 4H), 1.46-1.27 (m, 2H) ppm. LCMS: R$_t$=0.897 min, MS+1=630.1. HPLC: R$_t$=2.348 min. SFC: R$_t$=1.789 min. (2S,3R)-2-(4-(cyclopentylamino)phenyl)-1-(2-fluoro-6-methylbenzoyl)-N-(4-methyl-3-(trifluoromethyl)phenyl)-1,2,3,4-tetrahydroquinoline-3-carboxamide was also produced as an off-white solid (7.49 mg, 24.4% yield, 97.8% purity). ¹H NMR: 400 MHz MeOD. δ 7.67-7.26 (m, 2H), 7.23-7.03 (m, 6H), 6.92-6.78 (m, 3H), 6.77-6.55 (m, 2H), 6.47-6.28 (m, 3H), 3.59-3.52 (m, 2H), 3.45-3.03 (m, 1H), 3.21-3.03 (m, 1H), 2.65-2.15 (m, 5.5H), 1.91-1.65 (m, 3.5H), 1.64-1.57 (m, 4H), 1.46-1.27 (m, 2H) ppm. LCMS: R$_t$=0.897 min, MS+1=630.1. HPLC, R$_t$=2.346 min. SFC: R$_t$=2.604 min.

Example 2

Synthesis of (2R,3S)-2-(4-(cyclopentylamino)phenyl)-1-(2-fluoro-6-methylbenzoyl)-N-(4-(hydroxymethyl)-3-(trifluoromethyl)phenyl)-1,2,3,4-tetrahydroquinoline-3-carboxamide (INF015)

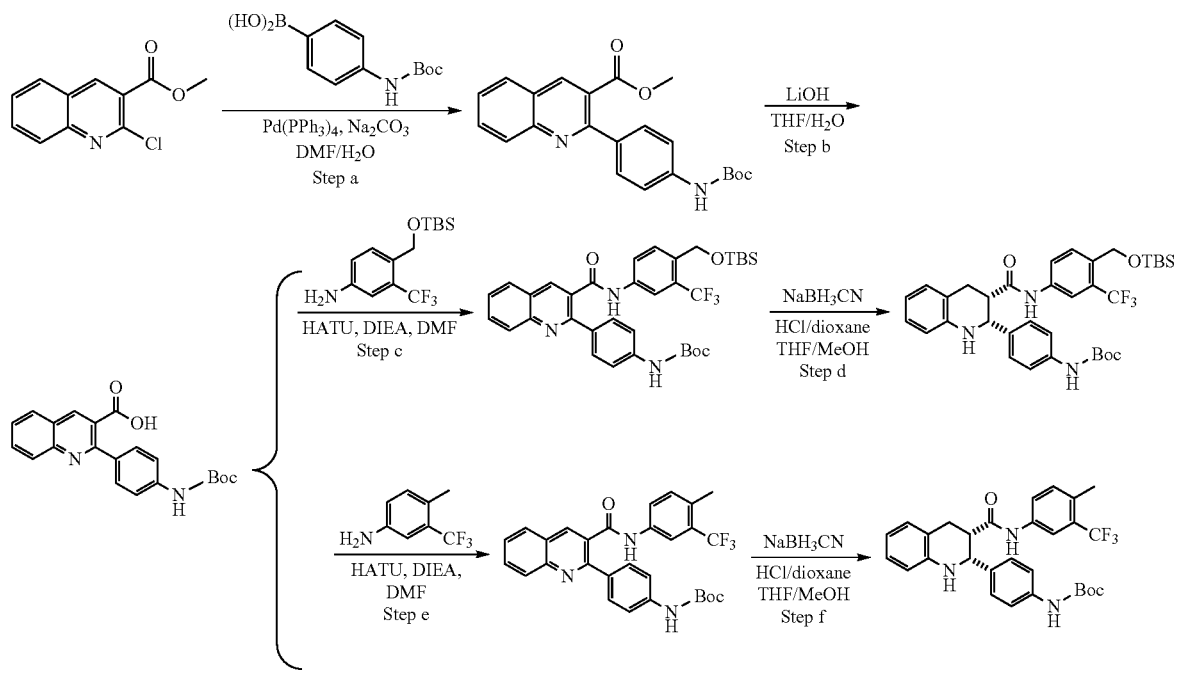

a) To a solution of methyl 2-chloroquinoline-3-carboxylate (25.0 g, 112 mmol) in DMF (250 mL) was added [4-(tert-butoxycarbonylamino)phenyl]boronic acid (32.0 g, 135 mmol). Na₂CO₃ (35.8 g, 338 mmol) in H₂O (100 mL) was then added followed by Pd(PPh₃)₄ (13.0 g, 11.2 mmol) was added. The mixture was stirred at 50° C. under N₂ for 5 hrs. Then Pd(dppf)Cl₂ (8.25 g, 11.2 mmol) was added. The mixture was stirred at 50° C. for 5 hrs. LCMS showed a small amount of starting material remained but a new major peak (R$_t$=0.975 min, MS+1=379.0) was formed. The reaction mixture was diluted with H₂O (1.20 L) and extracted with EtOAc 600 mL (300 mL×2). The combined organic layers were washed with brine 600 mL (300 mL×2), dried over Na₂SO₄, filtered and concentrated under reduced pressure to give a residue. The residue was purified by column chromatography (SiO₂, Petroleum ether/Ethyl acetate=10/1 to 2:1). Methyl 2-(4-((tert-butoxycarbonyl)amino)phenyl) quinoline-3-carboxylate (30.0 g, 77.6 mmol, 68.8% yield) was obtained as a yellow solid which was confirmed by LCMS R$_t$=0.973 min, MS+1=379.1 b) A mixture of methyl 2-(4-((tert-butoxycarbonyl)amino) phenyl)quinoline-3-carboxylate (24.0 g, 63.4 mmol) and LiOH.H₂O (7.98 g, 190 mmol) in THF (240 mL) and H₂O (100 mL) was degassed and purged with N₂ 3 times, and then the mixture was stirred at 15° C. for 3 hrs under N₂ atmosphere. TLC (petroleum ether/ethyl acetate=1:1) indicated that the starting material (R$_f$=0.5) was consumed completely and one new spot (R$_f$=0.05) formed. The reaction mixture was adjusted to pH=3~4 with HCl (1 M), the solid was filtered and concentrated under reduced pressure to give 2-(4-((tert-butoxycarbonyl)amino)phenyl)quinoline-3-carboxylic acid (15.7 g, 43.2 mmol, 68.1% yield) as a white solid which was confirmed by LCMS $R_t$=0.857 min, MS+1=365.0.

c) To a mixture of 2-(4-((tert-butoxycarbonyl)amino)phenyl)quinoline-3-carboxylic acid (4.50 g, 12.4 mmol), 4-(((tert-butyldimethylsilyl)oxy)methyl)-3-(trifluoromethyl)aniline (5.66 g, 18.5 mmol, 2.13 mL) and DIEA (3.99 g, 30.9 mmol, 5.38 mL) in DMF (40.0 mL) was added HATU (6.10 g, 16.1 mmol). The reaction mixture was stirred at 2030° C. for 15 hrs. LCMS showed the reaction was complete with the formation of the desired product (MS ($R_t$=1.036 min, MS+1=652.2)). The reaction mixture was poured into water (200 mL) and an off-white solid precipitated. The mixture was filtered. The filter cake was triturated with Petroleum ether:EtOAc=4: 1 (50.0 mL) to give tert-butyl (4-(3-((4-(((tert-butyldimethylsilyl)oxy)methyl)-3-(trifluoromethyl)phenyl)carbamoyl)quinolin-2-yl)phenyl)carbamate (6.50 g, 9.97 mmol, 80.7% yield) as an off-white solid which was confirmed by LCMS: $R_t$=1.036 min MS+1=652.2 and $^1$H NMR: 400 MHz DMSO-d$_6$ δ=10.9 (s, 1H), 9.51 (s, 1H), 8.66 (s, 1H), 8.11-8.09 (m, 2H), 8.05 (s, 1H), 8.04-7.87 (m, 2H), 7.71-7.69 (m, 4H), 7.68-7.53 (m, 2H), 4.81 (s, 2H), 1.47 (s, 9H), 0.91 (s, 9H), 0.10 (s, 6H) ppm.

d) To a mixture of tert-butyl (4-(3-((4-(((tert-butyldimethylsilyl)oxy)methyl)-3-(trifluoromethyl)phenyl)carbamoyl)quinolin-2-yl)phenyl)carbamate (6.50 g, 9.97 mmol) in THF (60 mL) and MeOH (30.0 mL) was added NaBH$_3$CN (2.51 g, 39.9 mmol) at 15° C. The mixture was adjusted to pH=5~6 with HCl/dioxane (4 M). The mixture was stirred at 1530° C. for 1 hr. TLC (Petroleum ether:EtOAc=3:1) showed the reaction was complete and two spots ($R_f$=0.7 and 0.6) were found. The reaction mixture was adjusted to pH=8~9 with saturated NaHCO$_3$, and then concentrated in vacuum. The residue was diluted with water (100 mL), extracted with EtOAc (200 mL). The organic phase was dried over Na$_2$SO$_4$, filtered and concentrated in vacuum. The residue was triturated with Petroleum ether:EtOAc=6:1 (70 mL) to give the desired cis compound (4.20 g, 5.89 mmol, 59.1% yield) as an off-white solid. LCMS: $R_t$=1.336 min MS+1=656.6. HPLC: $R_t$=5.241 min. $^1$H NMR: 400 MHz CDCl$_3$ δ=8.61 (s, 1H), 7.63 (d, J=8.6 Hz, 1H), 7.56 (d, J=2.0 Hz, 1H), 7.33 (dd, J=1.8, 8.4 Hz, 1H), 7.13-7.11 (m, 4H), 7.28-7.10 (m, 2H), 6.79-6.76 (m, 2H), 6.49 (s, 1H), 4.82 (s, 2H), 4.71 (d, J=3.2 Hz, 1H), 4.32 (s, 1H), 3.38 (dd, J=6.8, 16.9 Hz, 1H), 3.24 (td, J=3.4, 6.7 Hz, 1H), 3.16-3.11 (m, 1H), 1.51 (s, 9H), 0.94 (s, 9H), 0.06 (s, 6H) ppm.

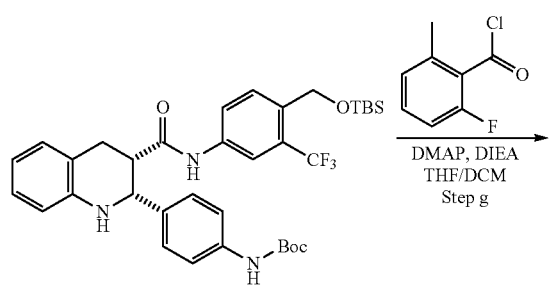

g) To a mixture of 2-fluoro-6-methylbenzoyl chloride (1.05 g, 6.10 mmol, 336 µL) in DCM (5.00 mL) was added a solution of the compound obtained above in Step d) (800 mg, 1.22 mmol), DMAP (45 mg, 368 µmol) and DIEA (960 mg, 7.43 mmol, 1.29 mL) in THF (10.0 mL) at 15° C. The reaction mixture was stirred at 1525° C. for 30 hrs. LCMS showed 13.1% of the starting material ($R_t$=1.235 min) remained along with the desired product MS ($R_t$=1.271 min). The reaction mixture was quenched by water (50.0 mL), extracted with DCM (100 mL), the organic phase was separated, washed with brine (100 mL), dried over Na$_2$SO$_4$, filtered and concentrated in vacuum to give the desired compound (1.80 g, crude) as a black oil which was used directly in next step. LCMS: $R_t$=1.271 min MS+46=837.4 h) To a mixture of the compound obtained above in Step g) (1.80 g, 2.27 mmol) in EtOAc (15.0 mL) was added HCl/dioxane (4 M, 15.0 mL). The reaction mixture was stirred at 15° C. for 2 hrs. LCMS showed the reaction was complete and the desired MS ($R_t$=0.860 min) was found. The reaction mixture was concentrated in vacuum. The residue was purified by Prep_HPLC (0.1% TFA) to give the target compound (126 mg, 13.6% yield for 2 steps) as a yellow foam which was confirmed by LCMS. LCMS: $R_t$=0.860 min MS+1=578.2.

i, j, k) To a mixture of the compound obtained above in Step h) (53 mg, 91.8 µmol) and cyclopentanone (62 mg, 737 mol, 65.3 µL) in MeOH (1.00 mL) was added AcOH (1 mg, 16.7 µmol, 0.95 µL) (Step i)). The reaction mixture was stirred at 15° C. for 1 hr before NaBH$_3$CN (30 mg, 478 µmol) was added and the mixture was stirred at 15° C. for 0.5 hr (Step j)). LCMS showed the reaction complete and the desired MS ($R_t$=0.929 min) was found. The reaction mixture was quenched by water (10.0 mL), extracted with EtOAc (20.0 mL). The organic phase was separated, dried over Na$_2$SO$_4$, filtered and concentrated in vacuum. The residue was purified by prep HPLC (TFA condition). The collected moving phase was concentrated in vacuum and the residue was adjusted to pH=8 with NaHCO$_3$ (solid), and extracted with EtOAc (20.0 mL). The organic phase was separated, dried over Na$_2$SO$_4$, filtered and concentrated in vacuum. In Step k), the residue was separated by SFC (column: DAICEL CHIRALCEL OJ-H (250 mm×30 mm, 5 µm); mobile phase: [0.1% NH$_3$H$_2$O MEOH]; B %: 25%-25%, 4.9 min; 60 min) to give the target compound, (2R,3S)-2-(4-(cyclopentylamino)phenyl)-1-(2-fluoro-6-methylbenzoyl)-N-(4-(hydroxymethyl)-3-(trifluoromethyl)phenyl)-1,2,3,4-tetrahydroquinoline-3-carboxamide (10 mg, 14.3 µmol, 31.1% yield, as an off-white solid. LCMS: $R_t$=0.828 min MS+1=646.1. HPLC: $R_t$=2.138 min. SFC: $R_t$=1.356 min. $^1$H NMR: 400 MHz DMSO-d$_6$. δ=10.7 (s, 1H), 8.11-8.01 (m 1H), 7.98-7.96 (m, 1H), 7.87-7.85 (m, 1H), 7.50-6.82 (m, 2H), 6.57-6.53 (m, 1H), 6.42-6.31 (m, 2H), 5.60-5.38 (m, 2H), 4.67 (s, 2H), 3.67-3.47 (m, 2H), 3.35-3.14 (m, 2H), 2.51 (s, 2H), 2.02 (s, 1H), 1.87-1.86 (m, 2H), 1.67-1.55 (m, 4H), 1.45-1.40 (m, 2H) ppm. F NMR: 400 MHz DMSO-d$_6$. δ=−59.138, −116.17 ppm. (2S,3R)-2-(4-(cyclopentylamino)phenyl)-1-(2-fluoro-6-methylbenzoyl)-N-(4-(hydroxymethyl)-3-(trifluoromethyl)phenyl)-1,2,3,4-tetrahydroquinoline-3-carboxamide was also produced (10 mg, 15.33 µmol, 33.4% yield) as an off-white solid. LCMS $R_t$=0.828 min MS+1=646.2. HPLC: $R_t$=2.142 min. SFC: $R_t$=1.485 min. $^1$H NMR: 400 MHz DMSO-d$_6$. δ=10.60 (br s, 1H), 7.92 (br d, J=9.5 Hz, 1H), 7.87-7.77 (m, 1H), 7.75-7.63 (m, 1H), 7.44-6.65 (m, 8H), 6.58-6.46 (m, 1H), 6.41-6.26 (m, 2H), 5.58-5.26 (m, 2H), 4.62 (br s, 2H), 3.55 (m, 2H), 3.30-2.97 (m, 2H), 2.47 (s, 2H), 1.97 (s, 1H), 1.82 (m, 2H), 1.67-1.41 (m, 4H), 1.34 (m, 2H) ppm. F NMR: 400 MHz DMSO-d$_6$. δ=−59.135, −116.17 ppm.

Example 3

Synthesis of (2R,3S)-1-(2-fluoro-6-methylbenzoyl)-N-(4-methyl-3-(trifluoromethyl)phenyl)-2-(4-((tetrahydro-2H-pyran-4-yl)amino)phenyl)-1,2,3,4-tetrahydroquinoline-3-carboxamide (INF011)

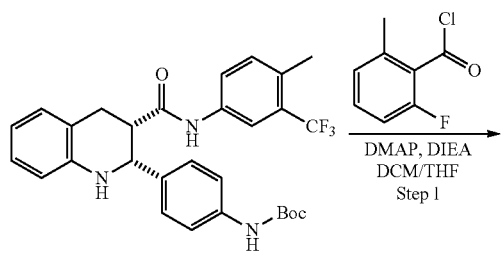

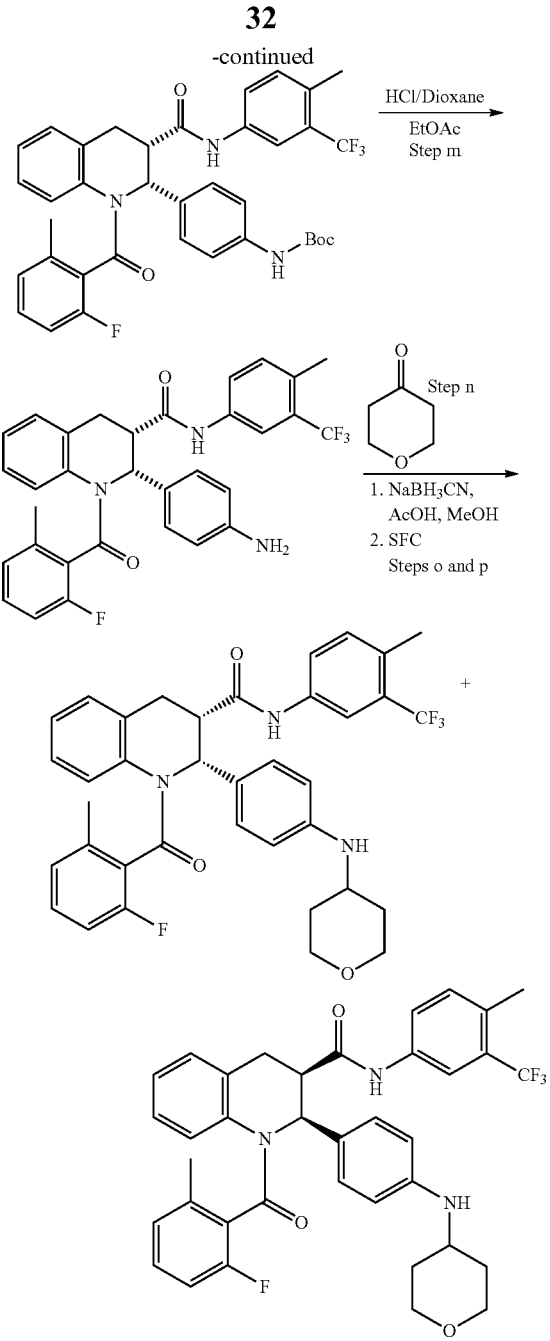

By replacing 4-(((tert-butyldimethylsilyl)oxy)methyl)-3-(trifluoromethyl)aniline in Example 2 Step c above with 4-methyl-3-(trifluoromethyl)aniline (Step e) gave the desired product tert-butyl (4-(3-((4-methyl-3-(trifluoromethyl)phenyl)carbamoyl)quinolin-2-yl)phenyl)carbamate (5.20 g, 9.97 mmol, yield 80.7%). Then reducing the product (Step f) gave cis tert-butyl (4-(3-((4-methyl-3-(trifluoromethyl)phenyl)carbamoyl)-1,2,3,4-tetrahydroquinolin-2-yl)phenyl)carbamate (3.10 g, 5.78 mmol, 58.0% yield) as a white solid. LCMS: $R_t$=1.181 min MS+1=526.5. HPLC: $R_t$=4.132 min. $^1$H NMR: 400 MHz CDCl$_3$. δ=8.50 (s, 1H), 7.45-7.42 (m, 2H), 7.35-7.28 (m, 4H), 7.13 (t, J=7.9 Hz, 3H), 6.85-6.75 (m, 2H), 6.47 (s, 1H), 4.71 (d, J=3.2 Hz, 1H), 4.32 (s, 1H), 3.39-3.37 (m, 1H), 3.24-3.21 (m, 1H), 3.16-3.11 (m, 1H), 2.39 (d, J=1.2 Hz, 3H), 1.52 (s, 9H) ppm.

l) To a solution of 2-fluoro-6-methylbenzoyl chloride (1.32 g, 7.65 mmol) in DCM (30.0 mL) was added a solution of cis tert-butyl (4-(3-((4-methyl-3-(trifluoromethyl)phenyl)carbamoyl)-1,2,3,4-tetrahydroquinolin-2-yl)phenyl)carbamate (1.00 g, 1.90 mmol), DIEA (1.24 g, 9.59 mmol, 1.67 mL) and DMAP (80 mg, 655 µmol) in DCM (30 mL) at 15° C. The reaction mixture was stirred at 15-30° C. for 10 hrs. LCMS showed 14% of starting material ($R_t$=1.081 min) remained along with the desired product MS ($R_t$=1.132 min). The reaction was quenched by water (100 mL), extracted with EtOAc (100 mL×2). The organic phase was separated, dried over $Na_2SO_4$, filtered and concentrated in vacuum. The residue was purified by prep_HPLC (0.1% TFA) to give the target compound (1.00 g, 1.51 mmol, 79.4% yield) as a yellow solid. LCMS: $R_t$=1.132 min MS+23=684.2.

m) To a solution of the compound obtained above in Step 1) (1.00 g, 1.51 mmol) in EtOAc (5.00 mL) was added HCl/Dioxane (4 M, 5.00 mL). The reaction mixture was stirred at 20° C. for 2 hrs. LCMS showed the reaction was complete and the desired MS ($R_t$=0.908 min) was found. The reaction mixture was concentrated in vacuum. The residue was dissolved in EtOAc (50.0 mL), washed with saturated $NaHCO_3$ (50.0 mL), separated, dried over $Na_2SO_4$, filtered and concentrated in vacuum to give the target (803 mg, 1.43 mmol, 94.6% yield) as a yellow foam. LCMS: $R_t$=0.908 min MS+1=562.2.

n, o, p) To a mixture of the compound obtained above in Step m) (200 mg, 356 µmol) and tetrahydropyran-4-one (286 mg, 2.86 mmol, 262 µL) in MeOH (2.00 mL) was added AcOH (3 mg, 50.0 µmol, 2.86 µL) (Step n)). The reaction mixture was stirred at 15° C. for 1 hr. Then $NaBH_3CN$ (115 mg, 1.83 mmol) (Step o) was added and the mixture was stirred at 15° C. for 1 hr. LCMS showed the reaction was complete and the desired compound MS ($R_t$=0.985 min) was found. The reaction mixture was quenched by water (50.0 mL), extracted with EtOAc (50.0 mL). The organic phase was separated, dried over $Na_2SO_4$, filtered and concentrated in vacuum. The residue was separated by SFC (column: DAICEL CHIRALCEL OJ-H (250 mm×30 mm, 5 µm); mobile phase: [0.1% $NH_3H_2O$ MEOH]; B %: 25%-25%, 4.3 min; 60 min) (Step p) to give (2R,3S)-1-(2-fluoro-6-methylbenzoyl)-N-(4-methyl-3-(trifluoromethyl)phenyl)-2-(4-((tetrahydro-2H-pyran-4-yl)amino)phenyl)-1,2,3,4-tetrahydroquinoline-3-carboxamide (8 mg, 12.1 µmol, 6.78% yield) as a white solid which was confirmed by LCMS, $R_t$=0.885 min MS+1=646.3. HPLC, $R_t$=2.261 min. SFC: $R_t$=0.763 min. $^1$H NMR: 400 MHz DMSO-$d_6$. δ=10.55 (br s, 1H), 7.91 (d, J=1.6 Hz, 1H), 7.77-7.61 (m, 1H), 7.43-7.13 (m, 5H), 7.05-6.95 (m, 1H), 6.91-6.69 (m, 3H), 6.55-6.26 (m, 4H), 5.45 (t, J=8.0 Hz, 1H), 3.80 (br d, J=11.6 Hz, 2H), 3.63-3.49 (m, 1H), 3.31-2.99 (m, 4H), 2.46 (s, 2H), 2.39 (s, 3H), 1.96 (s, 1H), 2.01-1.93 (m, 1H), 1.80-1.70 (m, 2H), 1.31-1.24 (m, 2H) ppm. $^{19}$F NMR: 400 MHz DMSO-$d_6$ δ=−60.48, −116.19. (2S,3R)-1-(2-fluoro-6-methylbenzoyl)-N-(4-methyl-3-(trifluoromethyl)phenyl)-2-(4-((tetrahydro-2H-pyran-4-yl)amino)phenyl)-1,2,3,4-tetrahydroquinoline-3-carboxamide was also produced (8 mg, 12.0 µmol, 6.76% yield) as a white solid which was confirmed by LCMS $R_t$=0.884 min MS+1=646.2. HPLC: $R_t$=2.265 min. SFC: $R_t$=2.263 min. $^1$H NMR: 400 MHz DMSO-$d_6$ δ=10.55 (br s, 1H), 7.91 (br d, J=11.2 Hz, 1H), 7.77-7.61 (m, 1H), 7.43-7.13 (m, 5H), 7.05-6.95 (m, 1H), 6.91-6.69 (m, 3H), 6.55-6.26 (m, 4H), 5.45 (t, J=8.0 Hz, 1H), 3.80 (br d, J=11.6 Hz, 2H), 3.63-3.49 (m, 1H), 3.31-2.99 (m, 4H), 2.46 (s, 2H), 2.39 (s, 3H), 1.96 (s, 1H), 2.01-1.93 (m, 1H), 1.80-1.70 (m, 2H), 1.31-1.24 (m, 2H) ppm. $^{19}$F NMR: 400 MHz DMSO-$d_6$ δ=−60.48, −116.19.

Example 4

Synthesis of (2R,3S)-1-(2-chlorobenzoyl)-2-(4-(cyclopentylamino)phenyl)-N-(4-(hydroxymethyl)-3-(trifluoromethyl)phenyl)-1,2,3,4-tetrahydroquinoline-3-carboxamide (INF014)

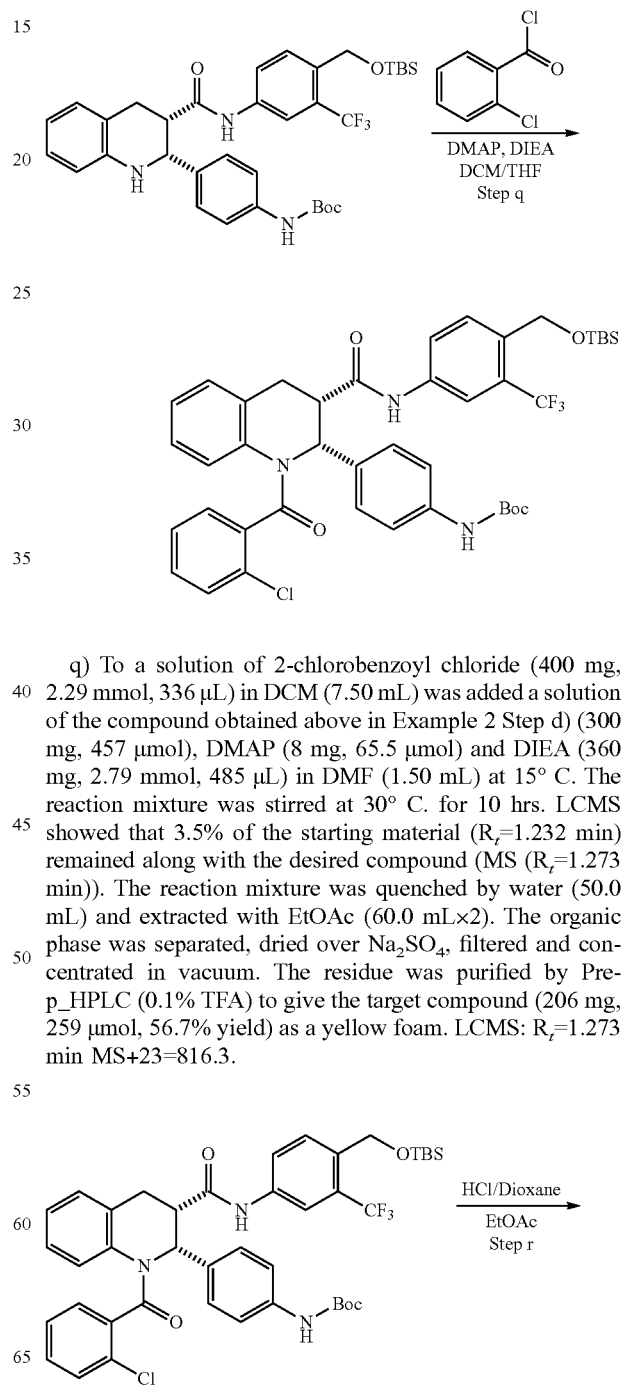

q) To a solution of 2-chlorobenzoyl chloride (400 mg, 2.29 mmol, 336 µL) in DCM (7.50 mL) was added a solution of the compound obtained above in Example 2 Step d) (300 mg, 457 µmol), DMAP (8 mg, 65.5 µmol) and DIEA (360 mg, 2.79 mmol, 485 µL) in DMF (1.50 mL) at 15° C. The reaction mixture was stirred at 30° C. for 10 hrs. LCMS showed that 3.5% of the starting material ($R_t$=1.232 min) remained along with the desired compound (MS ($R_t$=1.273 min)). The reaction mixture was quenched by water (50.0 mL) and extracted with EtOAc (60.0 mL×2). The organic phase was separated, dried over $Na_2SO_4$, filtered and concentrated in vacuum. The residue was purified by Prep_HPLC (0.1% TFA) to give the target compound (206 mg, 259 µmol, 56.7% yield) as a yellow foam. LCMS: $R_t$=1.273 min MS+23=816.3.

-continued

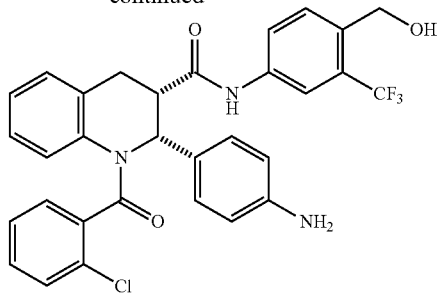

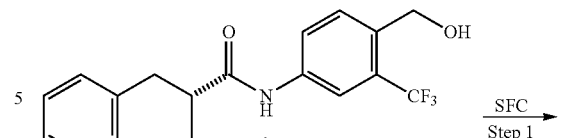

r) To a solution of the compound obtained above in Step q) (206 mg, 297 μmol) in EtOAc (3.00 mL) was added HCl/dioxane (4 M, 3 mL). The reaction mixture was stirred at 15° C. for 2 hrs. LCMS showed the reaction was completed and the desired compound MS ($R_t$=0.891 min) was found. The reaction mixture was concentrated in vacuum. The residue was dissolved in EtOAc (50 mL), washed with saturated NaHCO$_3$ (50.0 mL). The organic phase was separated, dried over Na$_2$SO$_4$, filtered and concentrated in vacuum to give the target compound (151 mg, 260 μmol, 87.7% yield) as a yellow foam. LCMS: $R_t$=0.891 min MS+1=580.1.

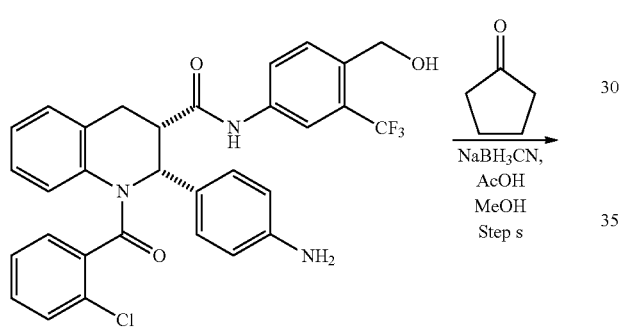

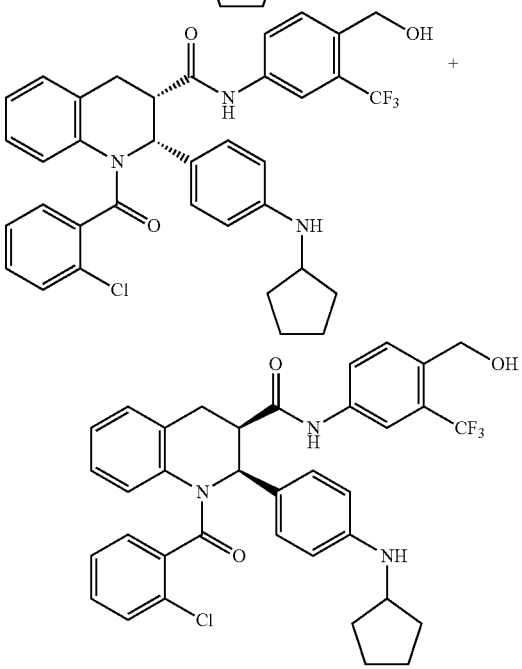

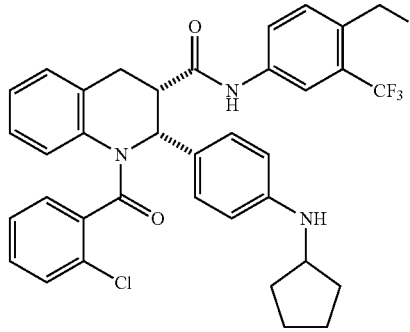

s) To a solution of the compound obtained above in Step r) (153 mg, 264 μmol) and cyclopentanone (220 mg, 2.62 mmol, 232 μL) in MeOH (2.00 mL) was added AcOH (5 mg, 83.3 μmol, 4.76 μL). The reaction mixture was stirred at 20° C. for 1 hr before NaBH$_3$CN (85 mg, 1.35 mmol) was added and the mixture was stirred at 20° C. for 1 hr. LCMS showed the reaction was complete and the desired compound MS ($R_t$=0.908 min) was detected. The reaction mixture was quenched by water (10.0 mL), extracted with EtOAc (20.0 mL). The organic phase was separated, dried over Na$_2$SO$_4$, filtered and concentrated in vacuum. The residue was purified by Prep_HPLC (TFA) to give the target compound (73 mg, 107 μmol, 40.4% yield) as a white solid. LCMS: $R_t$=0.908 min MS+1=648.4. HPLC: $R_t$=2.035 min. SFC: $R_t$=0.614 and 1.031 min.

t) The compound obtained above in Step s) (73 mg, 112 μmol, 1.00 eq) was separated by SFC (column: DAICEL CHIRALPAK AD (250 mm×30 mm, 10 μm); mobile phase: [0.1% NH$_3$H$_2$O ETOH]; B %: 55%-55%, 3.2 min; 40 min) to give (2R,3S)-1-(2-chlorobenzoyl)-2-(4-(cyclopentylamino)phenyl)-N-(4-(hydroxymethyl)-3-(trifluoromethyl)phenyl)-1,2,3,4-tetrahydroquinoline-3-carboxamide (7 mg, 10.3 μmol, 18.2% yield) as a white solid which was confirmed by LCMS: $R_t$=0.827 min MS+1=648.1. HPLC: $R_t$=2.061 min. SFC: $R_t$=0.618 min. $^1$H NMR: 400 MHz DMSO-d$_6$. δ=10.6 (br s, 1H), 7.94 (s, 1H), 7.84 (br d, J=8.1 Hz, 1H), 7.70 (br d, J=8.3 Hz, 1H), 7.64-7.06 (m, 5H), 7.00 (br s, 1H), 6.89-6.52 (m, 3H), 6.46 (br d, J=8.3 Hz, 1H), 6.29 (br d, J=8.6 Hz, 2H), 5.48 (d, J=6.1 Hz, 1H), 5.41 (t, J=5.6 Hz, 1H), 4.62 (br d, J=5.4 Hz, 2H), 3.68 (br s, 1H), 3.60-3.47 (m, 1H), 3.31-2.99 (m, 2H), 1.92-1.73 (m, 2H), 1.68-1.42 (m, 4H), 1.36-1.31 (m, 2H) ppm. $^{19}$F NMR: 400 MHz DMSO-d$_6$ δ=−59.15. (2S,3R)-1-(2-chlorobenzoyl)-2-(4-(cyclopentylamino)phenyl)-N-(4-(hydroxymethyl)-3-trifluoromethyl)phenyl)-1,2,3,4-tetrahydroquinoline-3-carboxamide was also produced (7 mg, 10.8 μmol, 19.2% yield) as a white solid which was confirmed by LCMS: $R_t$=0.826 min MS+1=648.1. HPLC: $R_t$=2.056 min. SFC: $R_t$=1.010 min. $^1$H NMR: 400 MHz DMSO-d$_6$. δ=10.6 (br s, 1H), 7.94 (s, 1H), 7.84 (br d, J=8.1 Hz, 1H), 7.70 (br d, J=8.3 Hz, 1H), 7.64-7.06 (m, 5H), 7.00 (br s, 1H), 6.89-6.52 (m, 3H), 6.46 (br d, J=8.3 Hz, 1H), 6.29 (br d, J=8.6 Hz, 2H), 5.48 (d, J=6.1 Hz, 1H), 5.41 (t, J=5.6 Hz, 1H), 4.62 (br d, J=5.4 Hz, 2H), 3.68 (br s, 1H), 3.60-3.47 (m, 1H), 3.31-2.99 (m, 2H), 1.92-1.73 (m, 2H), 1.68-1.42 (m, 4H), 1.36-1.31 (m, 2H) ppm. $^{19}$F NMR: 400 MHz DMSO-$d_6$ δ=−59.15.

Example 5

Synthesis of (2R,3S,5R)-2-(4-(cyclopentylamino)phenyl)-1-(2,6-difluorobenzoyl)-N-(4-methyl-3-(trifluoromethyl)phenyl)-5-(trifluoromethyl)piperidine-3-carboxamide (INF056)

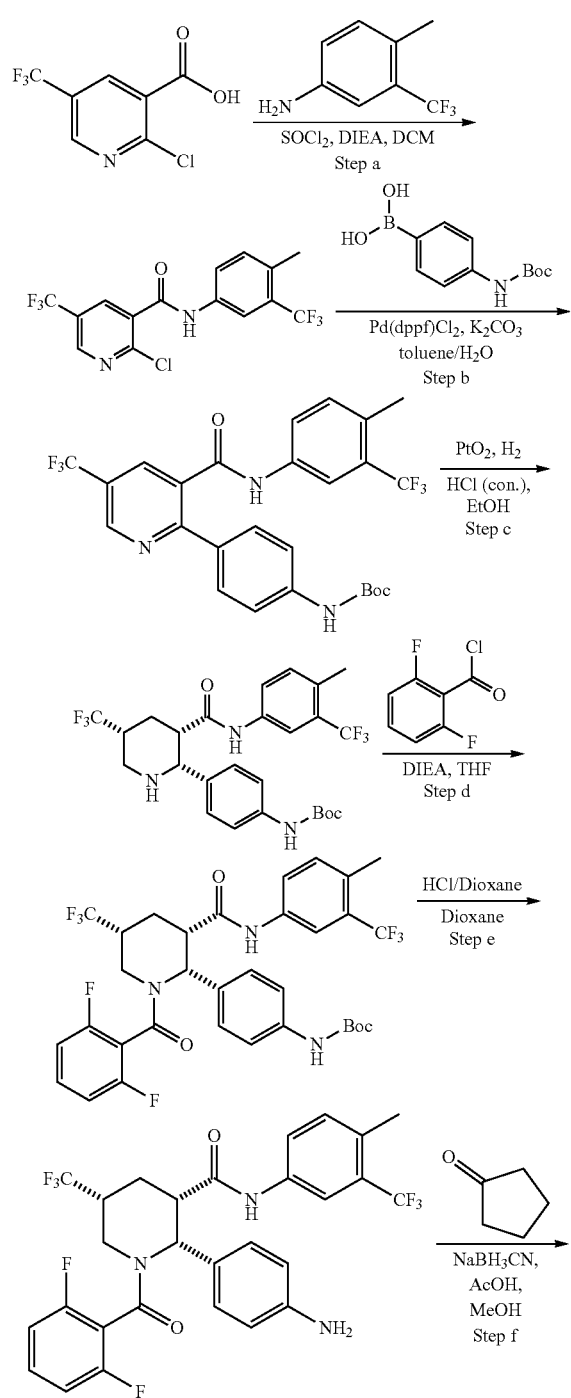

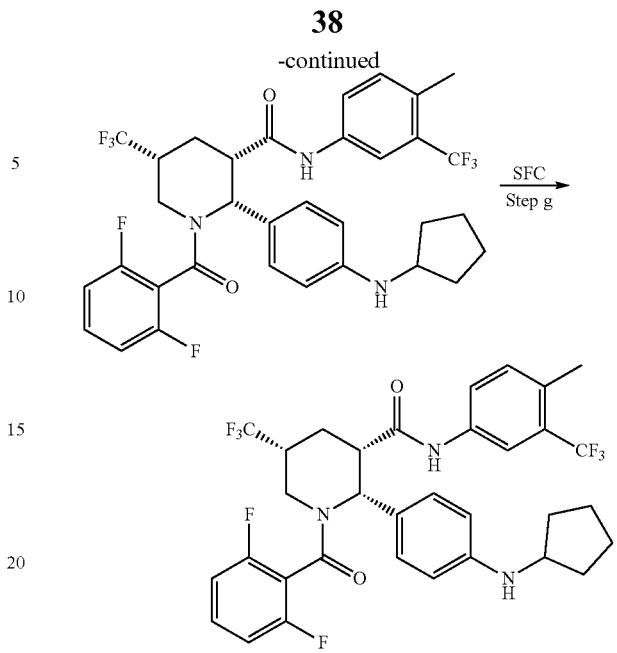

a) A mixture of 2-chloro-5-(trifluoromethyl)nicotinic acid (15.0 g, 66.5 mmol, 1.00 eq) in $SOCl_2$ (49.2 g, 413 mmol, 30.0 mL, 6.22 eq) was stirred at 90° C. for 1 hour, then the reaction mixture was concentrated under vacuum. The residue was dissolved with DCM (20.0 mL), and this solution was then added to a solution of compound 4-methyl-3-(trifluoromethyl)aniline (11.1 g, 63.2 mmol, 9.07 mL, 0.95 eq) in DIEA (25.8 g, 199 mmol, 34.7 mL, 3.00 eq) and DCM (100 mL). The resulting solution was stirred at 25° C. for 10 hours. LC-MS showed the desired mass was detected (RT=1.015 min, M+H$^+$: 383). The reaction mixture was quenched by addition NaHCO$_3$ (sat.) (100 mL), and then extracted with EtOAc (250 mL×2). The combined organic layers were washed with brine (200 mL×2), dried over Na$_2$SO$_4$, filtered and concentrated under reduced pressure to give the desired compound (25.0 g, crude) as a yellow solid.

b) To a mixture of the compound obtained above (25.0 g, 65.3 mmol, 1.00 eq) and (4-((tert-butoxycarbonyl)amino)phenyl)boronic acid (17.0 g, 71.7 mmol, 1.10 eq) in toluene (250 mL) was added a solution of K$_2$CO$_3$ (18.1 g, 131 mmol, 2.01 eq) in H$_2$O (50.0 mL) and Pd(dppf)Cl$_2$ (2.39 g, 3.27 mmol, 0.05 eq) under N$_2$. The mixture was stirred at 80° C. for 1 hour. LC-MS showed one main peak with the desired mass (RT=1.092 min, M+H$^+$: 540). The reaction mixture was quenched by the addition of H$_2$O (100 mL) and extracted with EtOAc (300 mL×2). The combined organic layers were washed with brine (200 mL), dried over Na$_2$SO$_4$, filtered and concentrated under reduced pressure to give a residue. The crude product was triturated with EtOAc (100 mL) at 25° C. for 30 min to the desired compound (29.0 g, 53.7 mmol, 82.3% yield) as a yellow solid.

c) To a mixture of the compound obtained above (6.00 g, 11.1 mmol, 1.00 eq) in EtOH (300 mL) was added PtO$_2$ (300 mg, 1.32 mmol, 1.19e-1 eq) and HCl (2.04 g, 20.1 mmol, 2.00 mL, 36.0% purity, 1.81 eq). The mixture was stirred at 25° C. for 12 hours under H$_2$ (15 Psi). LC-MS showed desired mass was detected (RT=0.908 min, M+H$^+$: 546). TLC (Petroleum ether:Ethyl acetate=3/1) indicated two new spots formed (R$_f$=0.5, 0.4). The residue was poured into NaHCO$_3$ (100 mL) (sat.) and the aqueous phase was extracted with ethyl acetate (300 mL×2). The combined organic phase was washed with brine (50.0 mL×2), dried with anhydrous Na$_2$SO$_4$, filtered and concentrated in vacuum. The residue was purified by column chromatography (SiO$_2$, Petroleum ether/Ethyl acetate=100/1 to 5/1) to give the desired compound (3.00 g, 5.50 mmol, 49.4% yield) as a white solid.

d) To a mixture of the compound obtained above (400 mg, 733 umol, 1.00 eq) in THF (6.00 mL) was added DIPEA (482 mg, 3.73 mmol, 649 uL, 5.09 eq) and 2,6-difluorobenzoyl chloride (518 mg, 2.93 mmol, 370 uL, 4.00 eq) in one portion under N$_2$. The mixture was stirred at 25° C. for 2 hours. LC-MS showed the desired mass was detected (RT=1.129 min, M+H$^+$: 686). TLC (Petroleum ether/Ethyl acetate=3/1) indicated a new spot formed (R$_f$=0.43). The reaction mixture was quenched by the addition of H$_2$O (10.0 mL), and then extracted with EtOAc (20.0 mL×2). The combined organic layers were washed with brine (10.0 mL), dried over Na$_2$SO$_4$, filtered and concentrated under reduced pressure to give a residue. The residue was purified by column chromatography (SiO$_2$, Petroleum ether/Ethyl acetate=100/1 to 10/1) to give the desired compound (400 mg, 583 umol, 79.6% yield) as a white solid.

e) To a mixture of the compound obtained above (200 mg, 291 umol, 1.00 eq) in dioxane (2.00 mL) was added HCl/dioxane (4 M, 5.00 mL, 68.5 eq) in one portion. The mixture was stirred at 25° C. for 1 hour. LC-MS showed the desired mass was detected (RT=0.959 min, M+H$^+$: 586). The reaction mixture was quenched by the addition of NaHCO$_3$ (sat.) (100 mL), and then extracted with EtOAc (50.0 mL×2). The combined organic layers were washed with brine (20.0 mL×2), dried over Na$_2$SO$_4$, filtered and concentrated under reduced pressure to give the desired compound (170 mg, crude) as a yellow solid.

f) To a mixture of the compound obtained above (170 mg, 290 umol, 1.00 eq) and cyclopentanone (73.0 mg, 867 umol, 76.8 uL, 2.99 eq) in MeOH (5.00 mL) was added AcOH (2.00 mg, 33.3 umol, 1.90 uL, 0.012 eq) in one portion. The mixture was stirred at 25° C. for 30 min, then NaBH$_3$CN (36.0 mg, 572 umol, 1.97 eq) was added to the reaction mixture. The resulting solution was stirred at 25° C. for 11.5 hrs. LC-MS showed the desired mass was detected (RT=1.052 min, M+H$^+$: 654). The reaction mixture was quenched by NaHCO$_3$ (sat.) (10.0 mL), and then extracted with EtOAc (20.0 mL×2). The combined organic layers were washed with brine (10.0 mL), dried over Na$_2$SO$_4$, filtered and concentrated under reduced pressure to give a residue. The residue was purified by prep-HPLC (column: Phenomenex Gemini-NX C18 75*30 mm*3 um; mobile phase: [water (0.1% TFA)-ACN]; B %: 52%-82%, 7 min) to give the desired compound (150 mg, 229 umol, 79.0% yield) as a yellow solid.

g) The compound obtained above (150 mg, 229 umol, 1.00 eq) was purified by SFC (column: DAICEL CHIRALCEL OJ-H (250 mm*30 mm, 5 um); mobile phase: [0.1% NH$_3$H$_2$O MEOH]; B %: 25%-25%, 3.65 min; 238 min). (2R,3S,5R)-2-(4-(cyclopentylamino)phenyl)-1-(2,6-difluorobenzoyl)-N-(4-methyl-3-(trifluoromethyl)phenyl)-5-(trifluoromethyl)piperidine-3-carboxamide (8.00 mg, 12.1 umol, 10.5% yield, 99.0% purity) was obtained as an off white solid. $^1$H NMR: (400 MHz, DMSO-d$_6$). δ 10.49 (s, 1H), 7.90 (s, 1H), 7.70-7.60 (m, 2H), 7.35-7.24 (m, 3H), 7.12 (d, J=8.4 Hz, 1.5H), 6.47-6.42 (m, 2.5H), 5.63 (d, J=6.4 Hz, 1H), 3.62-3.60 (m, 1H), 3.42-3.32 (m, 1H), 3.20-3.09 (m, 2H), 2.75-2.52 (m, 2H), 2.36 (s, 3H), 2.20-2.06 (m, 2H), 1.87-1.85 (m, 2H), 1.64-1.63 (m, 2H), 1.52-1.50 (m, 2H), 1.39-1.36 (m, 2H) ppm. F NMR: (400 MHz, DMSO-d$_6$) δ–60.528, –71.493, –114.098 ppm. LCMS: RT=1.042 min, M+H$^+$: 654. HPLC: RT=3.437 min. SFC: RT=0.878 min.

(2S,3R,5S)-2-(4-(cyclopentylamino)phenyl)-1-(2,6-difluorobenzoyl)-N-(4-methyl-3-(trifluoromethyl)phenyl)-5-(trifluoromethyl)piperidine-3-carboxamide (8.00 mg, 12.2 umol, 10.6% yield, 100% purity) was also obtained as a yellow solid. $^1$H NMR: (400 MHz, DMSO-d$_6$) δ 10.49 (s, 1H), 7.90 (s, 1H), 7.70-7.60 (m, 2H), 7.35-7.24 (m, 3H), 7.12 (d, J=8.4 Hz, 1.5H), 6.47-6.42 (m, 2.5H), 5.63 (d, J=6.4 Hz, 1H), 3.62-3.60 (m, 1H), 3.42-3.32 (m, 1H), 3.20-3.09 (m, 2H), 2.75-2.52 (m, 2H), 2.36 (s, 3H), 2.20-2.06 (m, 2H), 1.87-1.85 (m, 2H), 1.64-1.63 (m, 2H), 1.52-1.50 (m, 2H), 1.39-1.36 (m, 2H ppm). F NMR: (400 MHz, DMSO-d$_6$) δ–60.528, –71.493, –114.098 ppm. LCMS: RT=1.046 min, M+H$^+$: 654. HPLC: RT=3.440 min. SFC: RT=1.422 min.

Compounds (2R,3S,5R)-2-(4-(cyclopentylamino)phenyl)-1-(2-fluoro-6-methylbenzoyl)-N-(4-methyl-3-(trifluoromethyl)phenyl)-5-(trifluoromethyl)piperidine-3-carboxamide (INF056) and (2R,3S,5R)-2-(4-(cyclopentylamino)phenyl)-1-(2,6-dimethylbenzoyl)-N-(4-methyl-3-(trifluoromethyl)phenyl)-5-(trifluoromethyl)piperidine-3-carboxamide (INF053) were obtained in a similar manner.

B. Biological Assays

Calcium$^{++}$ Mobilization Assay

U937 cells (ATCC® CRL-1593.2) were cultivated in RPMI1640 medium supplemented with 10% fetal bovine serum in a standard cell culture incubator. The day before conducting the assay, Dibutyryl-cAMP (0.5 mM working concentration) was added to cell cultures. Next day, cells were spun and resuspended in RPMI 1640 to a concentration of 40,000 cells per 50 μl. 40,000 cells were plated in one well in a 96 well poly-D-lysine coated plate for two hours to allow cells to adhere. After cell adherence, cytoplasmic calcium$^{++}$ indicator (FLIPR Calcium 6 Assay Kit, Molecular Devices) was added to each well and incubated for 75 minutes at 37° C. Test compounds were diluted using a robotic liquid handler. The tips of the robotic liquid handler were changed after each mixing step. Test compounds were added into cell cultures at various concentrations (0.01 nM to 100 μM) for 15 minutes at 37° C. The cell culture plates were then incubated at room temperature for 30 minutes before being placed into Flexstation-3 plate reader (Molecular Devices). The Flexstation-3 was programmed to add recombinant C5a protein at various concentrations (1 nM to 10 nM) to cell culture plates and to monitor the change of fluorescence intensity, which correlates with cytoplasmic calcium concentration. The assay was also performed with the presence of human or animal blood components, such as human or bovine plasma or serum.

Chemotaxis Assay

U937 cells were cultivated in RPMI1640 medium supplemented with 10% fetal bovine serum in a standard cell culture incubator. The day before conducting the assay, Dibutyryl-cAMP (0.5 mM working concentration) was added to cell cultures. Next day cells were spun and resuspended in RPMI 1640 to a concentration of 50,000 cells per 20 μl. Cells were incubated with compounds at various concentrations (0.01 nM to 100 μM) for 30 minutes at 37° C. 50,000 cells in 20 μl of RPMI1640 were added into one well of upper chambers of a 96 well chemotaxis plate (the chemotaxis plates containing cell filters with 8 micrometer pores were purchased from Neuroprobe). C5a or other chemoattractants with preferred concentration in 29 μl of HBSS buffer were added into lower chambers. Cells migrated into lower chambers after one to three hours were stained using Cell Titer Glo (Invitrogen) and quantified using FlexStation® 3. The assay was also performed with the presence of human or animal blood components, such as human or bovine plasma or serum.

Beta-Arrestin Assay

U2OS (ATCC number HTB-96), an osteosarcoma cell line, was used to generate genetically engineered cell lines that overexpress two types of fusion proteins in the same cells: (a) fusion protein, TEV-C5aR1, which was composed of tobacco etch virus (TEV) protease fused to wild type human C5aR1 or human C5aR1 mutants. C5aR1 mutants carry mutations of amino acid(s) that was/were speculated to mediate the interaction between C5aR1 and test compounds. (b) fusion protein, Luc-arrestin, which was composed of β-arrestin-2, inactive permuted luciferase and a peptide constituting the TEV protease cleavage site. The peptide localized between β-arrestin-2 and luciferase.

The engineered U2OS cell lines were used to access the activity of C5aR1 and to what extent test compounds can modulate the activity of wild type or mutant C5aR1. In principle, C5a binding to C5aR1 portion of the TEV-C5aR1 at the cell surface activates C5aR1, leading to binding between the intracellular portion of TEV-C5aR1 to luc-arrestin inside cells, which allows TEV to cleave the peptide connecting beta-arrestin and luciferase. This cleavage converts inactive luciferase to active luciferase, which catalyzes added luciferase substrates and thus generates luminescence signals. The intensity of luminescence signals correlate with the activity of C5aR1.

Experimentally, engineered U2OS cells were cultivated in McCoy's medium supplemented with 10% fetal bovine serum in a standard cell culture incubator. Test compounds were added into cell culture medium and incubated for 30 minutes, followed by adding C5a into cell culture medium and incubating for one to three hours. Cells were then lysed by reagents containing luciferase substrates, such as One-glo or Bright-glo (Promega). The luminescence units (RLU) were recorded using a luminescence plate reader, such as FlexStation® 3 (Molecular Devices).

C5a-Induced CD11b Expression in Whole Blood Assay

Fresh peripheral blood samples are procured from consented human volunteers. 100 µl whole blood is incubated with test compounds with various concentrations (0.01 nM to 10 µM) for 20 minutes at 37° C. and then incubated with C5a with a preferred concentration ranging from 1 nM to 30 nM for 20 minutes at 37° C. The samples are ready for immunostaining followed by FACS (fluorescence activated cell sorting) analysis of CD11b expression by white blood cells. The samples are incubated with anti-CD11b antibody (BioLegend) on ice for 30 minutes protected from the light. One milliliter of Red Cell Lysis Buffer (Miltenyi) is added to 100 µl blood sample and incubated at room temperature for 10 minutes. Samples are washed using FACS staining buffer and resuspended in FACS buffer. Samples are analyzed by FACS (Beckman Coulter) for cell surface CD11b expression.

Animal Neutropenia Assay

Animals (mouse, rats or Mongolian gerbils) are acclimated for at least three days before being used for experiments. Test compounds (1 to 30 mg/kg) are administrated orally or intravenously. One to three hours later, animals are anaesthetized using a standard procedure, such as intraperitoneal administration of ketamine and xylazine. Animals are catheterized for C5a intravenous administration and blood collection. C5a is constituted in saline and injected intravenously at doses ranging from 30 µg/kg to 120 µg/kg. Blood samples are collected several times over 30 minutes after C5a administration. Blood samples are collected using heparin tubes. White blood cell differentials, such as abundance of neutrophils, in collected blood samples are analyzed by an automated blood cell analyzer (Siemens).

C. Results

The half maximal inhibitory concentrations, i.e. $IC_{50}$, were determined in biological assays, such as calcium mobilization assay. Using the calcium mobilization assay the following $IC_{50}$ values were determined by the best dose-response curve fitting method. The curves were plotted using percentage inhibition of C5a-induced calcium mobilization versus various concentrations of compounds.

| Chemical structure and short name of the compound | $IC_{50}$ |
|---|---|
| INF004 | <10 nM |
| INF011 | 100 nM - 1 µM |
| INF014 | 100 nM - 1 µM |

-continued
| Chemical structure and short name of the compound | IC$_{50}$ |
|---|---|
| 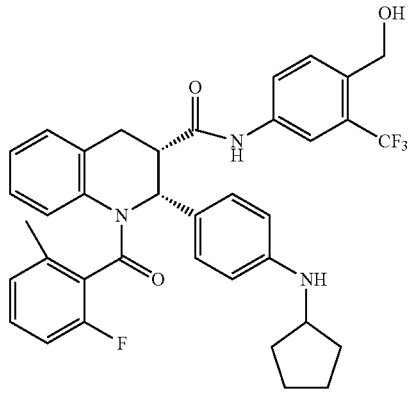 INF015 | <10 nM |
| 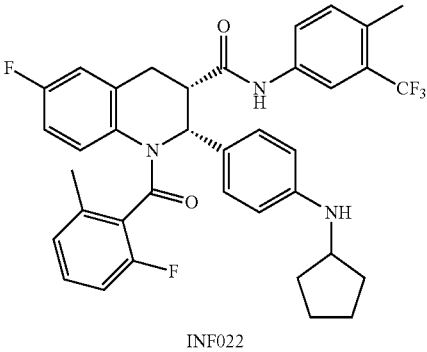 INF022 | <10 nM |
| 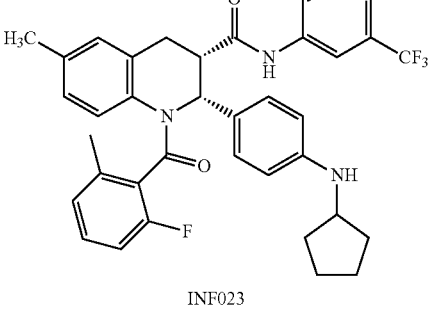 INF023 | <10 nM |
| 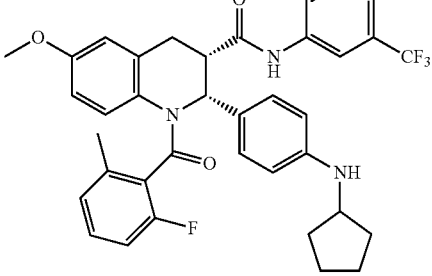 INF024 | <10 nM |
-continued
| Chemical structure and short name of the compound | IC$_{50}$ |
|---|---|
| 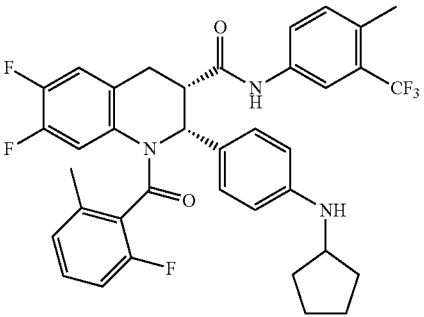 INF025 | 10 nM - 100 nM |
| 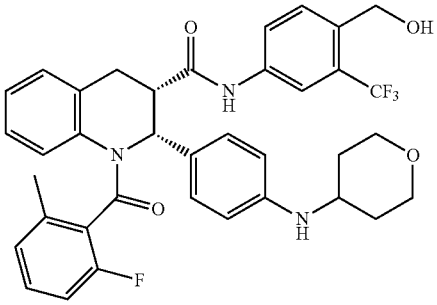 INF030 | 1 μM - 10 μM |
| 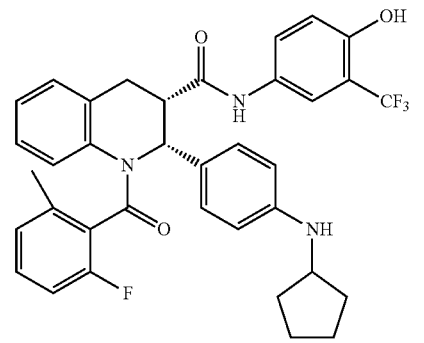 INF033 | <10 nM |
| 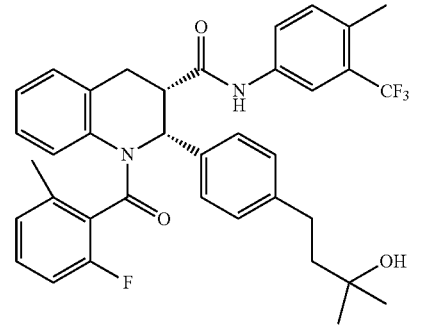 INF034 | 10 nM - 100 nM |

-continued
| Chemical structure and short name of the compound | IC$_{50}$ |
|---|---|
| 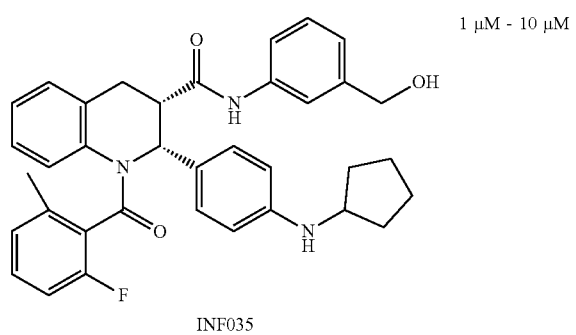 INF035 | 1 µM - 10 µM |
| 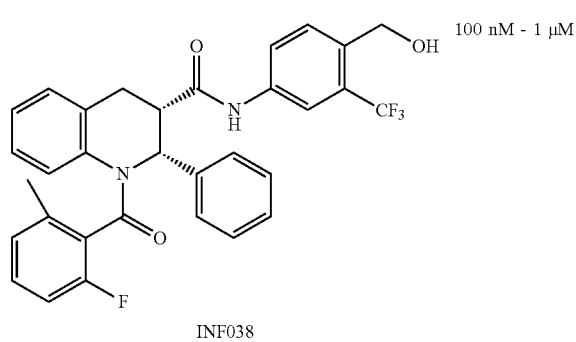 INF038 | 100 nM - 1 µM |
| 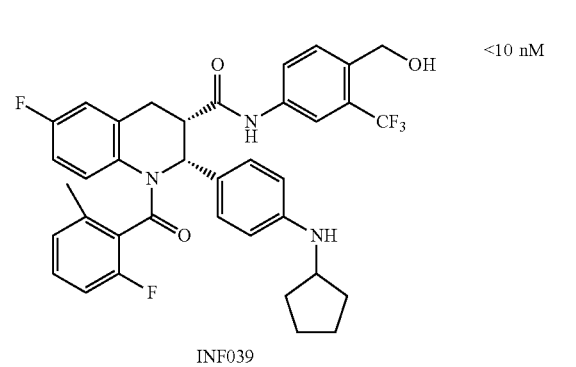 INF039 | <10 nM |
| 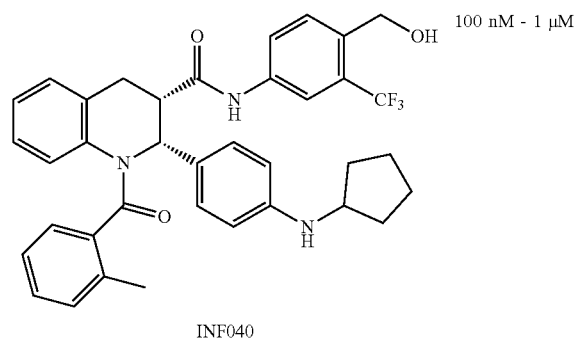 INF040 | 100 nM - 1 µM |
-continued
| Chemical structure and short name of the compound | IC$_{50}$ |
|---|---|
| 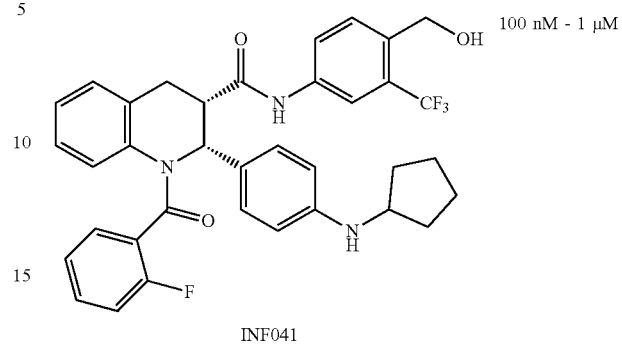 INF041 | 100 nM - 1 µM |
| 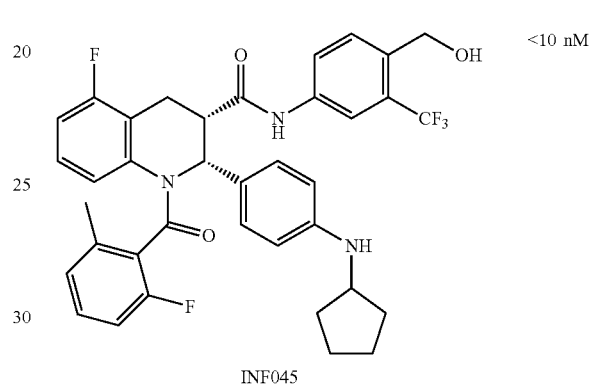 INF045 | <10 nM |
| 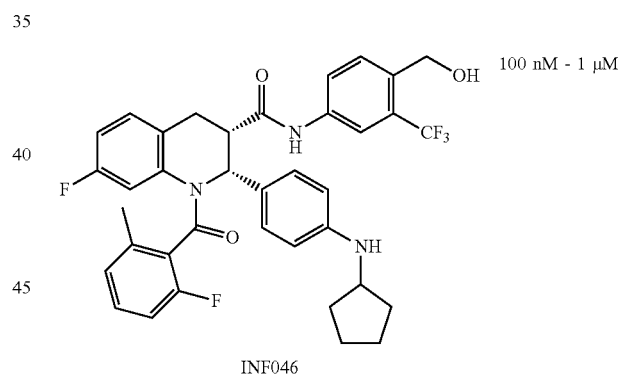 INF046 | 100 nM - 1 µM |
| 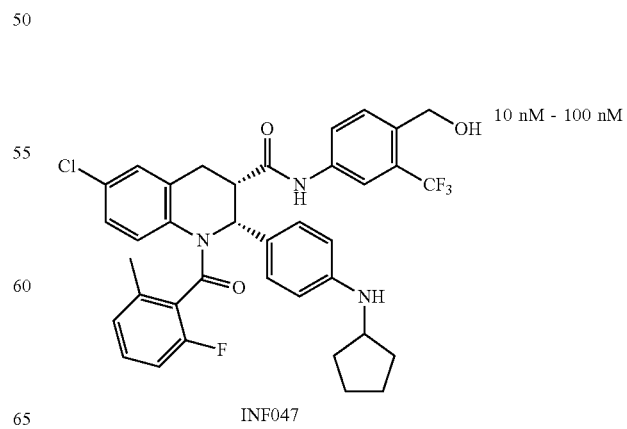 INF047 | 10 nM - 100 nM |

-continued
| Chemical structure and short name of the compound | IC$_{50}$ |
|---|---|
| 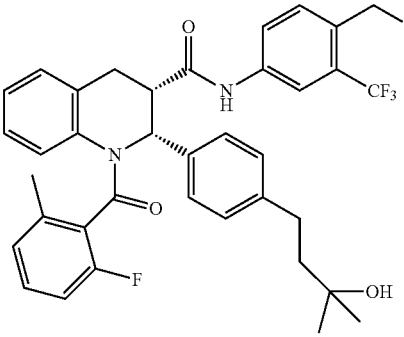 INF048 | 10 nM - 100 nM |
| 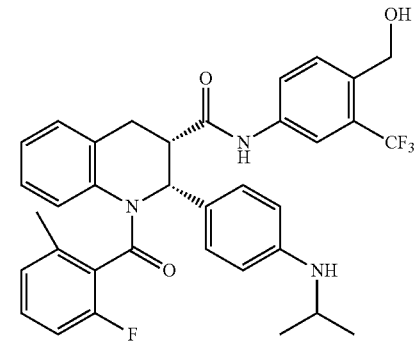 INF049 | 100 nM - 1 μM |
| 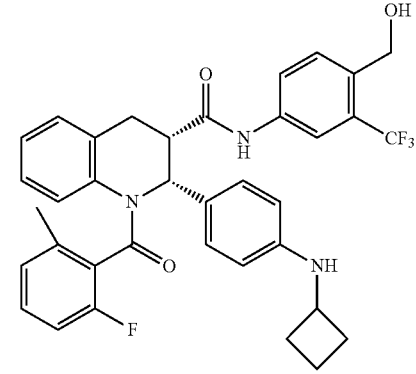 INF050 | 10 nM - 100 nM |
| 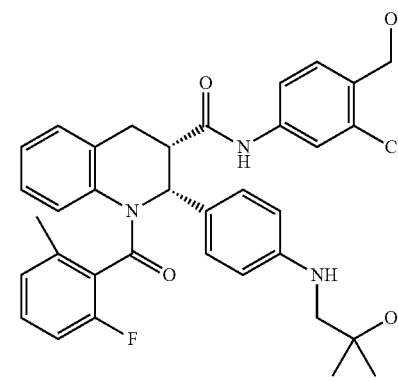 INF051 | 1 μM - 10 μM |
-continued
| Chemical structure and short name of the compound | IC$_{50}$ |
|---|---|
| 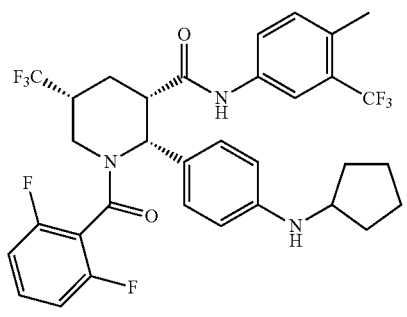 INF052 | <10 nM |
| 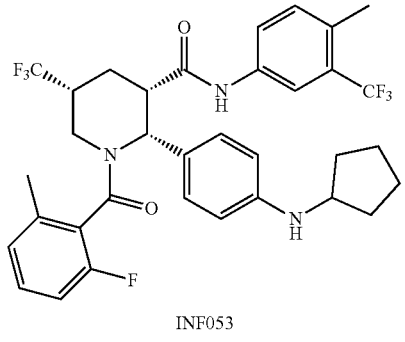 INF053 | <10 nM |
| 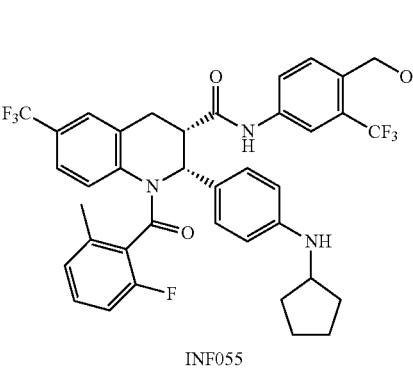 INF055 | 10 nM - 100 nM |
| 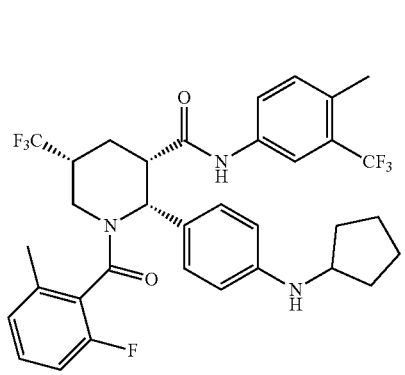 INF056 | 10 nM - 100 nM |

| Chemical structure and short name of the compound | IC$_{50}$ |
|---|---|
| 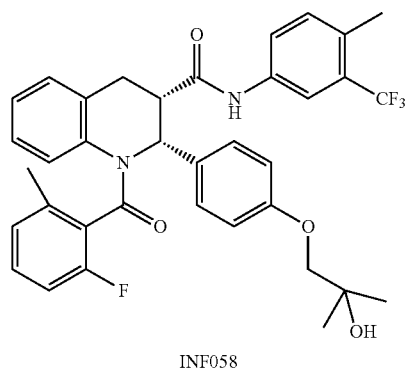<br>INF058 | 1 μM - 10 μM |
| 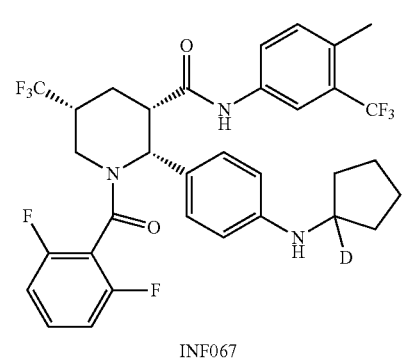<br>INF067 | <10 nM |
| 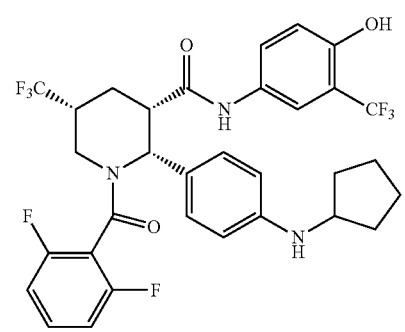<br>INF068 | <10 nM |
| 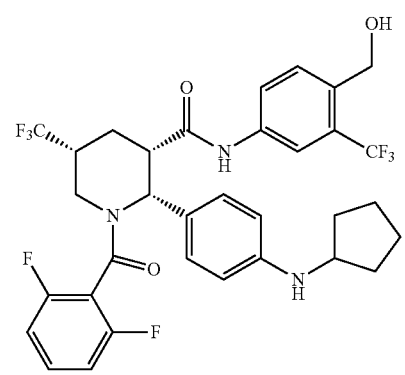<br>INF069 | 100 nM - 1 μM |
| 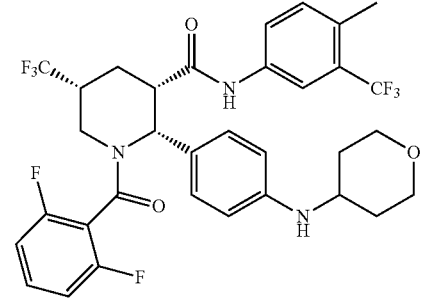<br>INF070 | 10 nM - 100 nM |
| 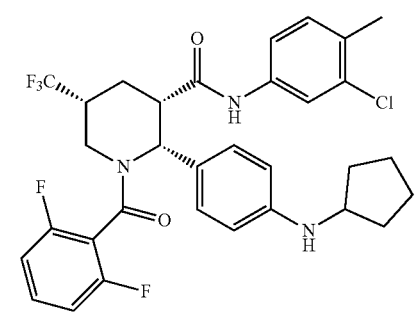<br>INF071 | <10 nM |
| 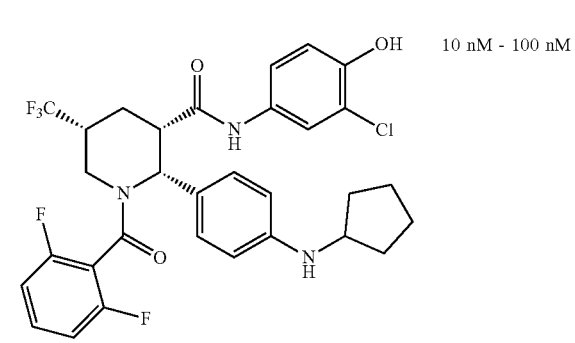<br>INF072 | 10 nM - 100 nM |
| 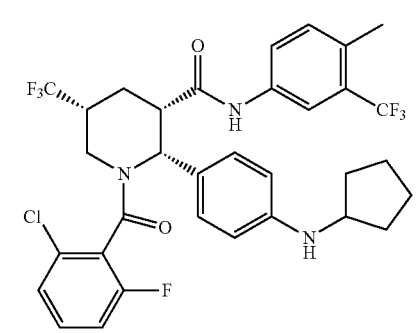<br>INF075 | 1 μM - 10 μM |

| Chemical structure and short name of the compound | IC$_{50}$ |
|---|---|
| 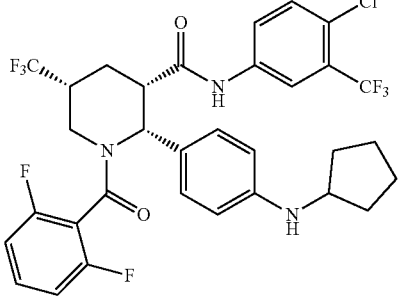<br>INF077 | 100 nM – 1 μM |
| 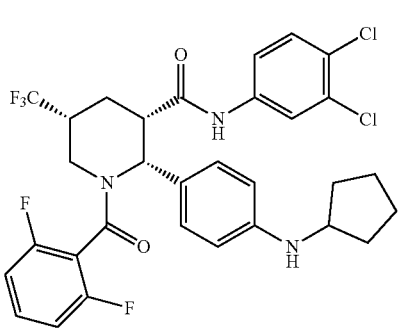<br>INF080 | 100 nM – 1 μM |

INF004: (2R,3S)-2-(4-(cyclopentylamino)phenyl)-1-(2-fluoro-6-methylbenzoyl)-N-(4-methyl-3-(trifluoromethyl)phenyl)-1,2,3,4-tetrahydroquinoline-3-carboxamide INF011: (2R,3S)-1-(2-fluoro-6-methylbenzoyl)-N-(4-methyl-3-(trifluoromethyl)phenyl)-2-(4-((tetrahydro-2H-pyran-4-yl)amino)phenyl)-1,2,3,4-tetrahydroquinoline-3-carboxamide INF014: (2R,3S)-1-(2-chlorobenzoyl)-2-(4-(cyclopentylamino)phenyl)-N-(4-(hydroxymethyl)-3-(trifluoromethyl)phenyl)-1,2,3,4-tetrahydroquinoline-3-carboxamide INF015: (2R,3S)-2-(4-(cyclopentylamino)phenyl)-1-(2-fluoro-6-methylbenzoyl)-N-(4-(hydroxymethyl)-3-(trifluoromethyl)phenyl)-1,2,3,4-tetrahydroquinoline-3-carboxamide INF022: (2R,3S)-2-(4-(cyclopentylamino)phenyl)-6-fluoro-1-(2-fluoro-6-methylbenzoyl)-N-(4-methyl-3-(trifluoromethyl)phenyl)-1,2,3,4-tetrahydroquinoline-3-carboxamide INF023: (2R,3S)-2-(4-(cyclopentylamino)phenyl)-1-(2-fluoro-6-methylbenzoyl)-6-methyl-N-(4-methyl-3-(trifluoromethyl)phenyl)-1,2,3,4-tetrahydroquinoline-3-carboxamide INF024: (2R,3S)-2-(4-(cyclopentylamino)phenyl)-1-(2-fluoro-6-methylbenzoyl)-6-methoxy-N-(4-methyl-3-(trifluoromethyl)phenyl)-1,2,3,4-tetrahydroquinoline-3-carboxamide INF025: (2R,3S)-2-(4-(cyclopentylamino)phenyl)-6,7-difluoro-1-(2-fluoro-6-methylbenzoyl)-N-(4-methyl-3-(trifluoromethyl)phenyl)-1,2,3,4-tetrahydroquinoline-3-carboxamide INF030: (2R,3S)-1-(2-fluoro-6-methylbenzoyl)-N-(4-(hydroxymethyl)-3-(trifluoromethyl)phenyl)-2-(4-((tetrahydro-2H-pyran-4-yl)amino)phenyl)-1,2,3,4-tetrahydroquinoline-3-carboxamide INF033: (2R,3S)-2-(4-(cyclopentylamino)phenyl)-1-(2-fluoro-6-methylbenzoyl)-N-(4-hydroxy-3-(trifluoromethyl)phenyl)-1,2,3,4-tetrahydroquinoline-3-carboxamide INF034: (2R,3S)-1-(2-fluoro-6-methylbenzoyl)-2-(4-(3-hydroxy-3-methylbutyl)phenyl)-N-(4-methyl-3-(trifluoromethyl)phenyl)-1,2,3,4-tetrahydroquinoline-3-carboxamide INF035: (2R,3S)-2-(4-(cyclopentylamino)phenyl)-1-(2-fluoro-6-methylbenzoyl)-N-(3-(hydroxymethyl)phenyl)-1,2,3,4-tetrahydroquinoline-3-carboxamide INF038: (2R,3S)-1-(2-fluoro-6-methylbenzoyl)-N-(4-(hydroxymethyl)-3-(trifluoromethyl)phenyl)-2-phenyl-1,2,3,4-tetrahydroquinoline-3-carboxamide INF039: (2R,3S)-2-(4-(cyclopentylamino)phenyl)-6-fluoro-1-(2-fluoro-6-methylbenzoyl)-N-(4-(hydroxymethyl)-3-(trifluoromethyl)phenyl)-1,2,3,4-tetrahydroquinoline-3-carboxamide INF040: (2R,3S)-2-(4-(cyclopentylamino)phenyl)-N-(4-(hydroxymethyl)-3-(trifluoromethyl)phenyl)-1-(2-methylbenzoyl)-1,2,3,4-tetrahydroquinoline-3-carboxamide INF041: (2R,3S)-2-(4-(cyclopentylamino)phenyl)-1-(2-fluorobenzoyl)-N-(4-(hydroxymethyl)-3-(trifluoromethyl)phenyl)-1,2,3,4-tetrahydroquinoline-3-carboxamide INF045: (2R,3S)-2-(4-(cyclopentylamino)phenyl)-5-fluoro-1-(2-fluoro-6-methylbenzoyl)-N-(4-(hydroxymethyl)-3-(trifluoromethyl)phenyl)-1,2,3,4-tetrahydroquinoline-3-carboxamide INF046: (2R,3S)-2-(4-(cyclopentylamino)phenyl)-7-fluoro-1-(2-fluoro-6-methylbenzoyl)-N-(4-(hydroxymethyl)-3-(trifluoromethyl)phenyl)-1,2,3,4-tetrahydroquinoline-3-carboxamide INF047: (2R,3S)-6-chloro-2-(4-(cyclopentylamino)phenyl)-1-(2-fluoro-6-methylbenzoyl)-N-(4-(hydroxymethyl)-3-(trifluoromethyl)phenyl)-1,2,3,4-tetrahydroquinoline-3-carboxamide INF048: (2R,3S)-1-(2-fluoro-6-methylbenzoyl)-2-(4-(3-hydroxy-3-methylbutyl)phenyl)-N-(4-(hydroxymethyl)-3-(trifluoromethyl)phenyl)-1,2,3,4-tetrahydroquinoline-3-carboxamide INF049: (2R,3S)-1-(2-fluoro-6-methylbenzoyl)-N-(4-(hydroxymethyl)-3-(trifluoromethyl)phenyl)-2-(4-(isopropylamino)phenyl)-1,2,3,4-tetrahydroquinoline-3-carboxamide INF050: (2R,3S)-2-(4-(cyclobutylamino)phenyl)-1-(2-fluoro-6-methylbenzoyl)-N-(4-(hydroxymethyl)-3-(trifluoromethyl)phenyl)-1,2,3,4-tetrahydroquinoline-3-carboxamide INF051: (2R,3S)-1-(2-fluoro-6-methylbenzoyl)-2-(4-((2-hydroxy-2-methylpropyl)amino)phenyl)-N-(4-(hydroxymethyl)-3-(trifluoromethyl)phenyl)-1,2,3,4-tetrahydroquinoline-3-carboxamide INF052: (2R,3S,5R)-2-(4-(cyclopentylamino)phenyl)-1-(2,6-difluorobenzoyl)-N-(4-methyl-3-(trifluoromethyl)phenyl)-5-(trifluoromethyl)piperidine-3-carboxamide INF053: (2R,3S,5R)-2-(4-(cyclopentylamino)phenyl)-1-(2,6-dimethylbenzoyl)-N-(4-methyl-3-(trifluoromethyl)phenyl)-5-(trifluoromethyl)piperidine-3-carboxamide INF055: (2R,3S)-2-(4-(cyclopentylamino)phenyl)-1-(2-fluoro-6-methylbenzoyl)-N-(4-(hydroxymethyl)-3-(trifluoromethyl)phenyl)-6-(trifluoromethyl)-1,2,3,4-tetrahydroquinoline-3-carboxamide INF056: (2R,3S,5R)-2-(4-(cyclopentylamino)phenyl)-1-(2-fluoro-6-methylbenzoyl)-N-(4-methyl-3-(trifluoromethyl)phenyl)-5-(trifluoromethyl)piperidine-3-carboxamide INF058: (2R,3S)-1-(2-fluoro-6-methylbenzoyl)-2-(4-(2-hydroxy-2-methyl)propoxy)phenyl)-N-(4-methyl-3-(trifluoromethyl)phenyl)-1,2,3,4-tetrahydroquinoline-3-carboxamide INF067: (2R,3S,5R)-2-(4-((cyclopentyl-1-d)amino)phenyl)-1-(2,6-difluorobenzoyl)-N-(4-methyl-3-(trifluoromethyl)phenyl)-5-(trifluoromethyl)piperidine-3-carboxamide INF068: (2R,3S,5R)-2-(4-(cyclopentylamino)phenyl)-1-(2,6-difluorobenzoyl)-N-(4-hydroxy-3-(trifluoromethyl)phenyl)-5-(trifluoromethyl)piperidine-3-carboxamide INF069: (2R,3S,5R)-2-(4-(cyclopentylamino)phenyl)-1-(2,6-difluorobenzoyl)-N-(4-(hydroxymethyl)-3-(trifluoromethyl)phenyl)-5-(trifluoromethyl)piperidine-3-carboxamide INF070: (2R,3S,5R)-1-(2,6-difluorobenzoyl)-N-(4-methyl-3-(trifluoromethyl)phenyl)-2-(4-((tetrahydro-2H-pyran-4-yl)amino)phenyl)-5-(trifluoromethyl)piperidine-3-carboxamide INF071: (2R,3S,5R)—N-(3-chloro-4-methylphenyl)-2-(4-(cyclopentylamino)phenyl)-1-(2,6-difluorobenzoyl)-5-(trifluoromethyl)piperidine-3-carboxamide INF072: (2R,3S,5R)—N-(3-chloro-4-hydroxyphenyl)-2-(4-(cyclopentylamino)phenyl)-1-(2,6-difluorobenzoyl)-5-(trifluoromethyl)piperidine-3-carboxamide INF075: (2R,3 S,5R)-1-(2-chloro-6-fluorobenzoyl)-2-(4-(cyclopentylamino)phenyl)-N-(4-methyl-3-(trifluoromethyl)phenyl)-5-(trifluoromethyl)piperidine-3-carboxamide INF077: (2R,3S,5R)—N-(4-chloro-3-(trifluoromethyl)phenyl)-2-(4-(cyclopentylamino)phenyl)-1-(2,6-difluorobenzoyl)-5-(trifluoromethyl)piperidine-3-carboxamide INF080: (2R,3S,5R)-2-(4-(cyclopentylamino)phenyl)-N-(3,4-dichlorophenyl)-1-(2,6-difluorobenzoyl)-5-(trifluoromethyl)piperidine-3-carboxamide

REFERENCES

1. Merle, N. S., et al., *Complement System Part I—Molecular Mechanisms of Activation and Regulation.* Front Immunol, 2015. 6: p. 262.
2. Schatz-Jakobsen, J. A., et al., *Structural and functional characterization of human and murine C5a anaphylatoxins.* Acta Crystallogr D Biol Crystallogr, 2014. 70 (Pt 6): p. 1704-17.
3. Klos, A., et al., *International Union of Basic and Clinical Pharmacology. [corrected]. LXXXVII. Complement peptide C5a, C4a, and C3a receptors.* Pharmacol Rev, 2013. 65(1): p. 500-43.
4. Ricklin, D., et al., *The renaissance of complement therapeutics.* Nat Rev Nephrol, 2018. 14(1): p. 26-47.
5. Tesar, V. and Z. Hruskova, *Avacopan in the treatment of ANCA-associated vasculitis.* Expert Opin Investig Drugs, 2018. 27(5): p. 491-496.
6. Li, G., et al., *Neuroprotective effects of argatroban and C5a receptor antagonist (PMX53) following intracerebral haemorrhage.* Clin Exp Immunol, 2014. 175(2): p. 285-95.
7. Nunez-Cruz, S., et al., *Genetic and pharmacologic inhibition of complement impairs endothelial cell function and ablates ovarian cancer neovascularization.* Neoplasia, 2012. 14(11): p. 994-1004.
8. Riedemann, N. C., et al., *Controlling the anaphylatoxin C5a in diseases requires a specifically targeted inhibition.* Clin Immunol, 2017. 180: p. 25-32.

The invention claimed is:
1. A compound selected from the group consisting of

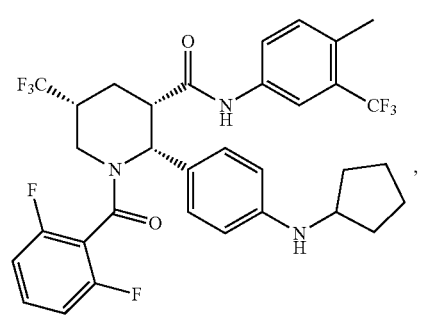

INF052

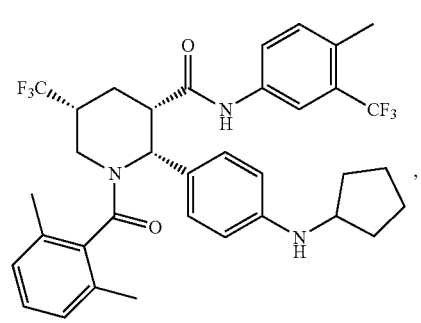

INF053

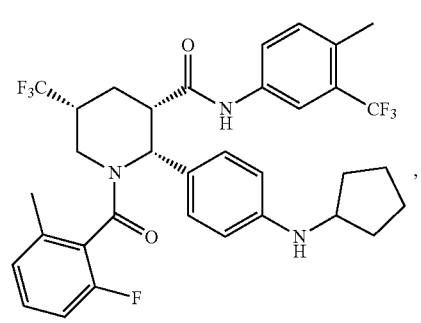

INF056

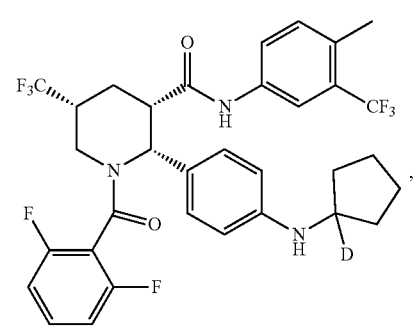

INF067

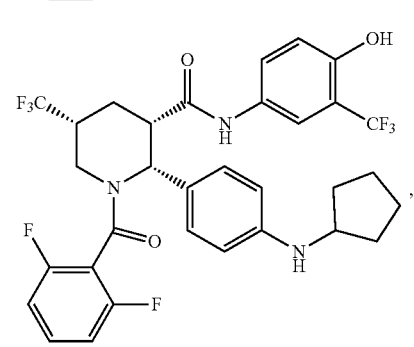

INF068

INF069
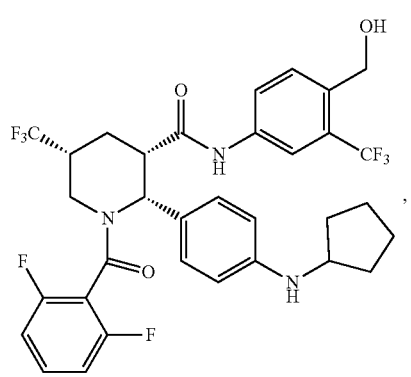
INF070
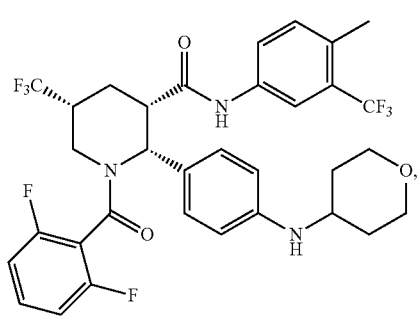
INF071
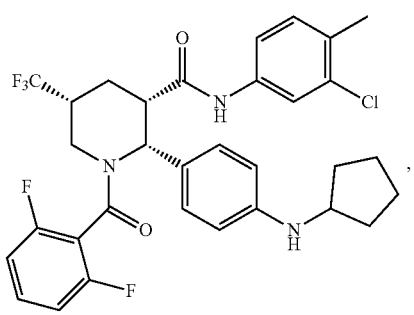
INF072
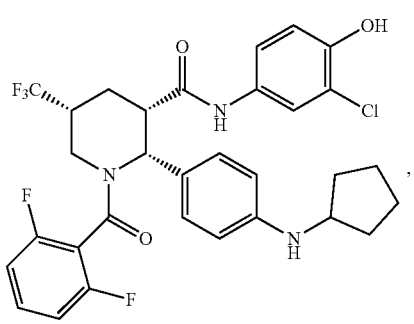
INF075
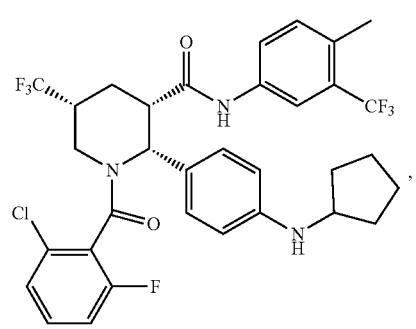
INF077
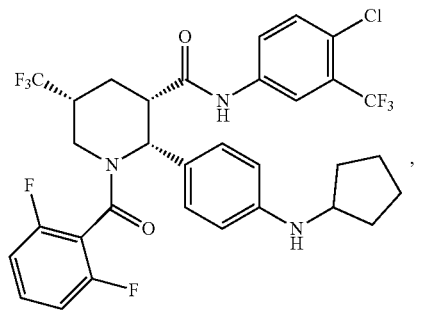
, and
INF080
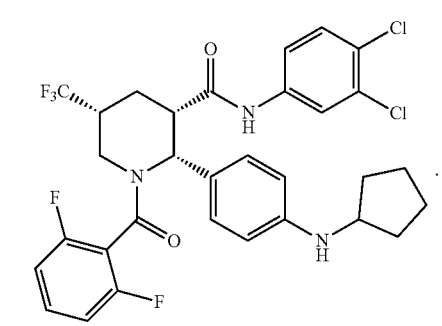
2. A pharmaceutical composition comprising a pharmaceutically acceptable carrier and the compound according to claim 1.
* * * * *